(12) United States Patent
Werneth et al.

(10) Patent No.: US 8,657,814 B2
(45) Date of Patent: Feb. 25, 2014

(54) USER INTERFACE FOR TISSUE ABLATION SYSTEM

(75) Inventors: Randell L. Werneth, San Diego, CA (US); J. Christopher Flaherty, Topsfield, MA (US); Hakan Oral, Ann Arbor, MI (US); Fred Morady, Ann Arbor, MI (US); Ricardo David Roman, San Diego, CA (US); Marshall L. Sherman, Cardiff By The Sea, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 874 days.

(21) Appl. No.: 11/438,678

(22) Filed: May 22, 2006

(65) Prior Publication Data
US 2007/0083193 A1  Apr. 12, 2007

Related U.S. Application Data

(60) Provisional application No. 60/710,451, filed on Aug. 22, 2005.

(51) Int. Cl.
*A61B 18/18* (2006.01)
(52) U.S. Cl.
USPC .................................. 606/41; 606/45; 606/32
(58) Field of Classification Search
USPC ............ 606/1, 32–42, 49; 600/300, 523, 525; 128/920, 922; 607/98–102, 113
See application file for complete search history.

(56) References Cited

U.S. PATENT DOCUMENTS

| 3,516,412 A | 6/1970 | Ackerman |
| 3,951,136 A | 4/1976 | Wall ........................ 128/2.06 E |
| 4,017,903 A | 4/1977 | Chu |
| 4,112,952 A | 9/1978 | Thomas et al. |
| 4,411,266 A | 10/1983 | Cosman |
| 4,432,377 A | 2/1984 | Dickhudt |
| 4,660,571 A | 4/1987 | Hess et al. |

(Continued)

FOREIGN PATENT DOCUMENTS

| AU | 5200671 | 10/2005 |
| CA | 2327322 | 11/1999 |

(Continued)

OTHER PUBLICATIONS

Oral et al., "Catheter ablation for paroxysmal atrial fibrillation: segmental pulmonary vein ostial ablation versus left atrial ablation," Circulation, vol. 108, pp. 2355-2360, 2003.

(Continued)

*Primary Examiner* — Linda Dvorak
*Assistant Examiner* — Amanda Scott
(74) *Attorney, Agent, or Firm* — Christopher & Weisberg, P.A.

(57) ABSTRACT

Devices, systems and methods are disclosed for the ablation of tissue. Embodiments include an ablation catheter that has an array of ablation elements attached to a deployable carrier assembly. The carrier assembly can be constrained within the lumen of a catheter, and deployed to take on an expanded condition. The carrier assembly includes multiple electrodes that are configured to ablate tissue at low power. Systems include an interface unit with a visual display that provides a visual representation of the geometry of the ablation elements and/or provides selection means for selecting an icon provided on the display.

16 Claims, 7 Drawing Sheets

(56) References Cited

U.S. PATENT DOCUMENTS

| | | | |
|---|---|---|---|
| 4,699,147 A | 10/1987 | Chilson et al. | |
| 4,785,815 A | 11/1988 | Cohen | |
| 4,860,769 A | 8/1989 | Fogarty et al. | |
| 4,869,248 A | 9/1989 | Narula | |
| 4,882,777 A | 11/1989 | Narula | |
| 4,896,671 A | 1/1990 | Cunningham et al. | |
| 4,907,589 A | 3/1990 | Cosman | |
| 4,920,980 A | 5/1990 | Jackowski | |
| 4,940,064 A | 7/1990 | Desai | |
| 4,966,597 A | 10/1990 | Cosman | |
| 5,010,894 A | 4/1991 | Edhag | 128/785 |
| 5,016,808 A | 5/1991 | Heil, Jr. et al. | |
| 5,083,565 A | 1/1992 | Parins | |
| 5,100,423 A | 3/1992 | Fearnot | |
| 5,156,151 A | 10/1992 | Imran | |
| 5,184,621 A | 2/1993 | Vogel et al. | 128/642 |
| 5,215,103 A | 6/1993 | Desai | |
| 5,228,442 A | 7/1993 | Imran | |
| 5,230,349 A | 7/1993 | Langberg | |
| 5,231,987 A * | 8/1993 | Robson | 607/29 |
| 5,231,995 A | 8/1993 | Desai | |
| 5,234,004 A | 8/1993 | Hascoet et al. | |
| 5,239,999 A | 8/1993 | Imran | |
| 5,255,679 A | 10/1993 | Imran | |
| 5,279,299 A | 1/1994 | Imran | |
| 5,281,213 A | 1/1994 | Milder et al. | |
| 5,281,218 A | 1/1994 | Imran | |
| 5,309,910 A * | 5/1994 | Edwards et al. | 600/381 |
| 5,313,943 A | 5/1994 | Houser et al. | |
| 5,318,525 A | 6/1994 | West et al. | |
| 5,324,284 A | 6/1994 | Imran | |
| 5,327,889 A | 7/1994 | Imran | |
| 5,330,466 A | 7/1994 | Imran | |
| 5,334,193 A | 8/1994 | Nardella | |
| 5,342,295 A | 8/1994 | Imran | |
| 5,342,357 A | 8/1994 | Nardella | |
| 5,345,936 A | 9/1994 | Pomeranz et al. | |
| 5,348,554 A | 9/1994 | Imran et al. | |
| D351,652 S | 10/1994 | Thompson et al. | |
| 5,364,352 A | 11/1994 | Cimino et al. | |
| 5,365,926 A | 11/1994 | Desai | |
| 5,370,644 A | 12/1994 | Langberg | |
| 5,383,917 A | 1/1995 | Desai et al. | |
| 5,391,147 A | 2/1995 | Imran et al. | |
| 5,397,304 A | 3/1995 | Truckai | |
| 5,397,339 A | 3/1995 | Desai | |
| 5,400,783 A | 3/1995 | Pomeranz et al. | |
| 5,404,638 A | 4/1995 | Imran | |
| 5,406,946 A | 4/1995 | Imran | |
| 5,411,025 A | 5/1995 | Webster, Jr. | |
| 5,423,808 A | 6/1995 | Edwards | |
| 5,423,811 A | 6/1995 | Imran et al. | |
| 5,433,198 A | 7/1995 | Desai | |
| 5,433,739 A * | 7/1995 | Sluijter et al. | 607/99 |
| 5,445,148 A | 8/1995 | Jaraczewski et al. | |
| 5,462,521 A | 10/1995 | Brucker et al. | |
| 5,462,545 A | 10/1995 | Wang | |
| 5,465,717 A | 11/1995 | Imran et al. | |
| 5,471,982 A | 12/1995 | Edwards et al. | |
| 5,487,757 A | 1/1996 | Truckai et al. | |
| 5,492,119 A | 2/1996 | Abrams | |
| 5,500,011 A | 3/1996 | Desai | |
| 5,507,802 A | 4/1996 | Imran | |
| 5,509,411 A | 4/1996 | Littmann et al. | |
| 5,527,279 A | 6/1996 | Imran | |
| 5,533,967 A | 7/1996 | Imran | |
| 5,536,267 A | 7/1996 | Edwards et al. | |
| 5,540,681 A | 7/1996 | Strul et al. | |
| 5,542,916 A * | 8/1996 | Hirsch et al. | 604/22 |
| 5,545,161 A | 8/1996 | Imran | |
| 5,545,193 A | 8/1996 | Fleischman et al. | |
| 5,545,200 A | 8/1996 | West et al. | |
| 5,558,073 A | 9/1996 | Pomeranz et al. | |
| 5,573,533 A | 11/1996 | Strul | |
| 5,575,766 A | 11/1996 | Swartz et al. | |
| 5,575,810 A | 11/1996 | Swanson et al. | |
| 5,578,007 A | 11/1996 | Imran | |
| 5,582,609 A | 12/1996 | Swanson et al. | |
| 5,584,830 A | 12/1996 | Ladd et al. | |
| 5,588,432 A * | 12/1996 | Crowley | 600/439 |
| 5,588,964 A | 12/1996 | Imran et al. | |
| 5,595,183 A | 1/1997 | Swanson et al. | |
| 5,596,995 A | 1/1997 | Sherman et al. | |
| 5,598,848 A | 2/1997 | Swanson et al. | |
| 5,601,088 A | 2/1997 | Swanson et al. | |
| 5,606,974 A | 3/1997 | Castellano et al. | |
| 5,607,462 A | 3/1997 | Imran | |
| 5,620,481 A | 4/1997 | Desai et al. | |
| 5,626,136 A | 5/1997 | Webster, Jr. | |
| 5,630,425 A | 5/1997 | Panescu et al. | |
| 5,630,837 A | 5/1997 | Crowley | |
| 5,637,090 A * | 6/1997 | McGee et al. | 604/95.01 |
| D381,076 S | 7/1997 | Thornton et al. | |
| 5,645,064 A | 7/1997 | Littmann et al. | |
| 5,645,082 A | 7/1997 | Sung et al. | |
| 5,656,029 A | 8/1997 | Imran et al. | |
| 5,657,755 A | 8/1997 | Desai | |
| 5,658,278 A | 8/1997 | Imran et al. | |
| 5,662,606 A | 9/1997 | Cimino et al. | |
| 5,666,970 A | 9/1997 | Smith | |
| 5,673,695 A * | 10/1997 | McGee et al. | 600/374 |
| 5,680,860 A | 10/1997 | Imran | |
| 5,681,280 A | 10/1997 | Rusk et al. | |
| 5,682,885 A | 11/1997 | Littmann et al. | |
| 5,685,322 A | 11/1997 | Sung et al. | |
| 5,687,723 A | 11/1997 | Avitall | |
| 5,693,078 A | 12/1997 | Desai et al. | |
| 5,697,927 A | 12/1997 | Imran et al. | |
| 5,697,928 A | 12/1997 | Walcott et al. | |
| 5,699,796 A | 12/1997 | Littmann et al. | |
| 5,702,438 A | 12/1997 | Avitall | |
| 5,704,791 A * | 1/1998 | Gillio | 434/262 |
| 5,706,809 A | 1/1998 | Littmann et al. | |
| 5,711,298 A | 1/1998 | Littmann et al. | |
| 5,716,389 A | 2/1998 | Walinsky et al. | |
| 5,722,401 A | 3/1998 | Pietroski et al. | |
| 5,722,975 A | 3/1998 | Edwards et al. | |
| 5,724,985 A * | 3/1998 | Snell et al. | 600/510 |
| 5,733,323 A | 3/1998 | Buck et al. | |
| 5,735,280 A | 4/1998 | Sherman et al. | |
| 5,741,320 A | 4/1998 | Thornton et al. | |
| 5,766,152 A | 6/1998 | Morley et al. | |
| 5,769,791 A * | 6/1998 | Benaron et al. | 600/473 |
| 5,769,847 A | 6/1998 | Panescu et al. | |
| 5,772,590 A | 6/1998 | Webster, Jr. | |
| 5,775,327 A | 7/1998 | Randolph et al. | |
| 5,782,239 A | 7/1998 | Webster, Jr. | |
| 5,782,760 A | 7/1998 | Schaer | |
| 5,782,828 A | 7/1998 | Chen et al. | |
| 5,782,899 A | 7/1998 | Imran | 607/122 |
| 5,792,140 A | 8/1998 | Tu et al. | |
| 5,800,482 A | 9/1998 | Pomeranz et al. | |
| 5,810,740 A | 9/1998 | Paisner | |
| 5,820,568 A * | 10/1998 | Willis | 600/523 |
| 5,827,272 A | 10/1998 | Breining et al. | |
| 5,837,001 A | 11/1998 | Mackey | |
| 5,849,028 A | 12/1998 | Chen | |
| 5,857,464 A | 1/1999 | Desai | |
| 5,857,997 A | 1/1999 | Cimino et al. | |
| 5,860,920 A | 1/1999 | McGee et al. | |
| 5,863,291 A | 1/1999 | Schaer | |
| 5,871,523 A | 2/1999 | Fleischman et al. | |
| 5,873,865 A | 2/1999 | Horzewski et al. | |
| 5,876,399 A | 3/1999 | Chia et al. | |
| 5,881,732 A | 3/1999 | Sung et al. | |
| 5,882,333 A | 3/1999 | Schaer et al. | |
| 5,885,278 A | 3/1999 | Fleischman | |
| 5,891,027 A | 4/1999 | Tu et al. | |
| 5,891,135 A | 4/1999 | Jackson et al. | |
| 5,891,137 A | 4/1999 | Chia et al. | |
| 5,891,138 A | 4/1999 | Tu et al. | |
| 5,893,847 A | 4/1999 | Kordis | |
| 5,893,884 A | 4/1999 | Tu | |
| 5,893,885 A | 4/1999 | Webster | |

(56) References Cited

U.S. PATENT DOCUMENTS

| | | | |
|---|---|---|---|
| 5,895,355 A | 4/1999 | Schaer | |
| 5,895,417 A | 4/1999 | Pomeranz et al. | |
| 5,897,554 A | 4/1999 | Chia et al. | |
| 5,904,680 A | 5/1999 | Kordis et al. | 606/41 |
| 5,906,605 A | 5/1999 | Coxum | |
| 5,910,129 A | 6/1999 | Koblish et al. | |
| 5,911,720 A | 6/1999 | Bourne et al. | 606/41 |
| 5,913,854 A | 6/1999 | Maguire et al. | |
| 5,916,214 A | 6/1999 | Cosio et al. | |
| 5,928,191 A | 7/1999 | Houser et al. | |
| 5,931,835 A | 8/1999 | Mackey | |
| 5,935,063 A | 8/1999 | Nguyen | |
| 5,938,694 A | 8/1999 | Jaraczewski et al. | |
| 5,941,845 A | 8/1999 | Tu | |
| 5,951,471 A | 9/1999 | de la Rama et al. | |
| 5,954,719 A | 9/1999 | Chen et al. | |
| 5,957,842 A | 9/1999 | Littmann et al. | |
| 5,960,796 A | 10/1999 | Sung et al. | |
| 5,967,978 A | 10/1999 | Littmann et al. | |
| 5,968,040 A | 10/1999 | Swanson et al. | 606/41 |
| 5,971,980 A | 10/1999 | Sherman | |
| 5,992,418 A | 11/1999 | de la Rama et al. | |
| 5,997,532 A | 12/1999 | McLaughlin et al. | |
| 6,001,093 A | 12/1999 | Swanson et al. | |
| 6,001,095 A | 12/1999 | de la Rama et al. | |
| 6,002,956 A | 12/1999 | Schaer | |
| 6,004,269 A | 12/1999 | Crowley et al. | 600/439 |
| 6,014,581 A * | 1/2000 | Whayne et al. | 600/523 |
| 6,021,340 A | 2/2000 | Randolph et al. | |
| 6,023,638 A * | 2/2000 | Swanson | 600/510 |
| 6,029,091 A | 2/2000 | de la Rama et al. | |
| 6,032,674 A | 3/2000 | Eggers et al. | 128/898 |
| 6,033,403 A | 3/2000 | Tu et al. | |
| 6,042,580 A | 3/2000 | Simpson | |
| 6,045,550 A | 4/2000 | Simpson et al. | |
| 6,048,329 A | 4/2000 | Thompson et al. | |
| 6,049,737 A | 4/2000 | Sherman | |
| 6,050,994 A | 4/2000 | Sherman | |
| 6,052,612 A | 4/2000 | Desai | |
| 6,053,937 A | 4/2000 | Edwards et al. | 607/104 |
| 6,056,744 A | 5/2000 | Edwards | |
| 6,059,778 A | 5/2000 | Sherman | |
| 6,063,077 A | 5/2000 | Schaer | |
| 6,063,082 A | 5/2000 | DeVore et al. | 606/45 |
| 6,064,902 A | 5/2000 | Haissaguerre et al. | |
| 6,068,629 A | 5/2000 | Haissaguerre et al. | |
| 6,070,094 A | 5/2000 | Swanson et al. | |
| 6,071,274 A | 6/2000 | Thompson et al. | |
| 6,071,279 A | 6/2000 | Whayne et al. | |
| 6,071,281 A * | 6/2000 | Burnside et al. | 606/41 |
| 6,071,282 A | 6/2000 | Fleischman | 606/41 |
| 6,074,351 A | 6/2000 | Houser | |
| 6,086,581 A | 7/2000 | Reynolds et al. | |
| 6,088,610 A | 7/2000 | Littmann et al. | |
| 6,096,036 A | 8/2000 | Bowe et al. | |
| 6,099,524 A | 8/2000 | Lipson et al. | |
| 6,106,522 A | 8/2000 | Fleischman et al. | |
| 6,107,699 A * | 8/2000 | Swanson | 307/112 |
| 6,115,626 A * | 9/2000 | Whayne et al. | 600/427 |
| 6,119,041 A | 9/2000 | Pomeranz et al. | |
| 6,120,476 A | 9/2000 | Fung et al. | |
| 6,129,724 A | 10/2000 | Fleischman et al. | |
| 6,141,576 A | 10/2000 | Littmann et al. | |
| 6,146,379 A | 11/2000 | Fleischman et al. | |
| 6,146,381 A | 11/2000 | Bowe et al. | |
| 6,165,169 A | 12/2000 | Panescu et al. | |
| 6,167,291 A | 12/2000 | Barajas et al. | |
| 6,171,305 B1 | 1/2001 | Sherman | |
| 6,171,306 B1 | 1/2001 | Swanson et al. | |
| 6,179,833 B1 | 1/2001 | Taylor | |
| 6,200,314 B1 | 3/2001 | Sherman | |
| 6,212,426 B1 * | 4/2001 | Swanson | 600/510 |
| 6,214,002 B1 | 4/2001 | Fleischman et al. | |
| 6,216,043 B1 | 4/2001 | Swanson et al. | |
| 6,216,044 B1 | 4/2001 | Kordis | |
| 6,217,573 B1 | 4/2001 | Webster | |
| 6,217,576 B1 | 4/2001 | Tu et al. | |
| 6,226,542 B1 | 5/2001 | Reisfeld | |
| 6,231,570 B1 | 5/2001 | Tu et al. | |
| 6,238,390 B1 | 5/2001 | Tu et al. | |
| 6,241,666 B1 | 6/2001 | Pomeranz et al. | |
| 6,241,724 B1 | 6/2001 | Fleischman et al. | |
| 6,241,725 B1 * | 6/2001 | Cosman | 606/41 |
| 6,241,726 B1 | 6/2001 | Raymond et al. | |
| 6,241,727 B1 | 6/2001 | Tu et al. | |
| 6,241,728 B1 | 6/2001 | Gaiser et al. | |
| 6,241,754 B1 | 6/2001 | Swanson et al. | |
| 6,245,067 B1 | 6/2001 | Tu et al. | |
| 6,245,089 B1 | 6/2001 | Daniel et al. | |
| 6,251,107 B1 | 6/2001 | Schaer | |
| 6,256,540 B1 | 7/2001 | Panescu et al. | |
| 6,264,664 B1 | 7/2001 | Avellanet | |
| 6,267,746 B1 | 7/2001 | Bumbalough | |
| 6,290,697 B1 | 9/2001 | Tu et al. | |
| 6,293,943 B1 | 9/2001 | Panescu et al. | |
| 6,302,880 B1 | 10/2001 | Schaer | |
| 6,309,385 B1 | 10/2001 | Simpson | |
| 6,312,425 B1 | 11/2001 | Simpson et al. | |
| 6,319,251 B1 | 11/2001 | Tu et al. | 606/41 |
| 6,325,797 B1 | 12/2001 | Stewart et al. | |
| 6,332,880 B1 | 12/2001 | Yang et al. | |
| 6,332,881 B1 | 12/2001 | Carner et al. | |
| 6,346,104 B2 | 2/2002 | Daly et al. | |
| 6,353,751 B1 | 3/2002 | Swanson | |
| 6,360,128 B2 | 3/2002 | Kordis et al. | |
| 6,370,435 B2 | 4/2002 | Panescu et al. | |
| 6,371,955 B1 | 4/2002 | Fuimaono et al. | |
| 6,379,352 B1 | 4/2002 | Reynolds et al. | |
| 6,389,311 B1 * | 5/2002 | Whayne et al. | 600/523 |
| 6,391,024 B1 | 5/2002 | Sherman | |
| 6,425,894 B1 | 7/2002 | Brucker et al. | |
| 6,428,536 B2 | 8/2002 | Panescu et al. | |
| 6,428,537 B1 * | 8/2002 | Swanson et al. | 606/41 |
| 6,440,129 B1 | 8/2002 | Simpson | |
| 6,447,506 B1 | 9/2002 | Swanson et al. | |
| 6,451,015 B1 * | 9/2002 | Rittman et al. | 606/34 |
| 6,454,758 B1 | 9/2002 | Thompson et al. | |
| 6,456,864 B1 | 9/2002 | Swanson et al. | |
| 6,460,545 B2 | 10/2002 | Kordis | |
| 6,471,693 B1 | 10/2002 | Carroll et al. | |
| 6,471,699 B1 | 10/2002 | Fleischman et al. | |
| 6,475,213 B1 | 11/2002 | Whayne et al. | |
| 6,475,214 B1 | 11/2002 | Moaddeb | |
| 6,477,396 B1 | 11/2002 | Mest et al. | |
| 6,478,793 B1 * | 11/2002 | Cosman et al. | 606/34 |
| 6,485,487 B1 | 11/2002 | Sherman | |
| 6,487,441 B1 | 11/2002 | Swanson et al. | |
| 6,488,678 B2 | 12/2002 | Sherman | |
| 6,490,468 B2 | 12/2002 | Panescu et al. | |
| 6,493,586 B1 * | 12/2002 | Stahmann et al. | 607/27 |
| 6,500,167 B1 | 12/2002 | Webster, Jr. | |
| 6,500,172 B1 | 12/2002 | Panescu et al. | |
| 6,514,246 B1 | 2/2003 | Swanson et al. | |
| 6,517,536 B2 | 2/2003 | Hooven et al. | |
| 6,522,905 B2 | 2/2003 | Desai | |
| 6,529,756 B1 | 3/2003 | Phan et al. | |
| 6,540,744 B2 | 4/2003 | Hassett et al. | |
| 6,542,773 B2 * | 4/2003 | Dupree et al. | 600/509 |
| 6,544,262 B2 | 4/2003 | Fleischman | 606/41 |
| 6,551,271 B2 | 4/2003 | Nguyen | |
| 6,554,794 B1 | 4/2003 | Mueller et al. | |
| 6,558,378 B2 | 5/2003 | Sherman | |
| 6,565,511 B2 | 5/2003 | Panescu et al. | |
| 6,569,114 B2 | 5/2003 | Ponzi et al. | |
| 6,569,162 B2 | 5/2003 | He | |
| 6,569,163 B2 * | 5/2003 | Hata et al. | 606/41 |
| 6,572,612 B2 | 6/2003 | Stewart et al. | |
| 6,574,492 B1 | 6/2003 | Ben-Haim et al. | |
| 6,575,997 B1 | 6/2003 | Palmer et al. | |
| 6,583,796 B2 * | 6/2003 | Jamar et al. | 715/804 |
| 6,597,955 B2 | 7/2003 | Panescu et al. | |
| 6,602,242 B1 | 8/2003 | Fung et al. | |
| 6,605,087 B2 | 8/2003 | Swartz et al. | |
| 6,607,505 B1 | 8/2003 | Thompson et al. | |

(56) References Cited

U.S. PATENT DOCUMENTS

| | | | |
|---|---|---|---|
| 6,607,520 B2 | 8/2003 | Keane | |
| 6,616,657 B2 | 9/2003 | Simpson et al. | |
| 6,625,482 B1 | 9/2003 | Panescu et al. | |
| 6,628,976 B1 | 9/2003 | Fuimaono et al. | |
| 6,632,223 B1 | 10/2003 | Keane | |
| 6,635,056 B2 | 10/2003 | Kadhiresan et al. | |
| 6,638,223 B2 * | 10/2003 | Lifshitz et al. | 600/440 |
| 6,638,275 B1 | 10/2003 | McGaffigan et al. | |
| 6,640,120 B1 | 10/2003 | Swanson et al. | |
| 6,652,513 B2 | 11/2003 | Panescu et al. | |
| 6,652,517 B1 | 11/2003 | Hall et al. | |
| 6,669,692 B1 | 12/2003 | Nelson et al. | |
| 6,669,693 B2 | 12/2003 | Friedman | |
| 6,671,533 B2 | 12/2003 | Chen et al. | |
| 6,690,972 B2 * | 2/2004 | Conley et al. | 607/31 |
| 6,701,180 B1 | 3/2004 | Desai | |
| 6,702,811 B2 | 3/2004 | Stewart et al. | |
| 6,711,428 B2 | 3/2004 | Fuimaono et al. | |
| 6,730,078 B2 * | 5/2004 | Simpson et al. | 606/34 |
| 6,738,673 B2 | 5/2004 | Desai | |
| 6,740,080 B2 | 5/2004 | Jain et al. | 606/34 |
| 6,743,225 B2 | 6/2004 | Sanchez et al. | |
| 6,746,446 B1 | 6/2004 | Hill et al. | |
| 6,761,716 B2 | 7/2004 | Sherman | |
| 6,805,131 B2 | 10/2004 | Kordis | |
| 6,813,520 B2 | 11/2004 | Truckai et al. | |
| 6,814,732 B2 | 11/2004 | Schaer | |
| 6,830,576 B2 | 12/2004 | Fleischman et al. | |
| 6,866,662 B2 | 3/2005 | Fuimaono et al. | |
| 6,893,438 B2 | 5/2005 | Hall et al. | |
| 6,893,439 B2 | 5/2005 | Fleischman | |
| 6,893,442 B2 | 5/2005 | Whayne | |
| 6,916,306 B1 | 7/2005 | Jenkins et al. | |
| 6,936,047 B2 | 8/2005 | Nasab et al. | |
| 6,939,349 B2 | 9/2005 | Fleischman et al. | |
| 6,952,615 B2 | 10/2005 | Satake | 607/102 |
| 6,955,173 B2 | 10/2005 | Lesh | |
| 6,960,206 B2 | 11/2005 | Keane | |
| 6,961,602 B2 | 11/2005 | Fuimaono et al. | |
| 6,964,660 B2 | 11/2005 | Maguire et al. | |
| 6,966,908 B2 | 11/2005 | Maguire et al. | |
| 6,972,016 B2 | 12/2005 | Hill, III et al. | |
| 6,973,339 B2 | 12/2005 | Govari | |
| 6,987,995 B2 | 1/2006 | Drysen | |
| 7,001,336 B2 | 2/2006 | Mandrusov et al. | |
| 7,025,766 B2 | 4/2006 | Whayne et al. | |
| 7,029,470 B2 | 4/2006 | Francischelli et al. | |
| 7,029,471 B2 | 4/2006 | Thompson et al. | |
| 7,044,135 B2 | 5/2006 | Lesh | |
| 7,047,068 B2 | 5/2006 | Haissaguerre | |
| 7,048,734 B1 | 5/2006 | Fleischman et al. | |
| 7,048,756 B2 | 5/2006 | Eggers et al. | |
| 7,077,823 B2 | 7/2006 | McDaniel | |
| 7,094,235 B2 | 8/2006 | Francischelli | |
| 7,099,711 B2 | 8/2006 | Fuimaono et al. | |
| 7,099,712 B2 | 8/2006 | Fuimaono et al. | |
| 7,113,831 B2 | 9/2006 | Hooven | |
| 7,115,122 B1 | 10/2006 | Swanson et al. | |
| 7,118,568 B2 | 10/2006 | Hassett et al. | |
| 7,122,031 B2 * | 10/2006 | Edwards et al. | 606/34 |
| 7,151,964 B2 | 12/2006 | Desai et al. | |
| 7,155,270 B2 | 12/2006 | Solis et al. | |
| 7,156,843 B2 | 1/2007 | Skarda | |
| 7,163,537 B2 | 1/2007 | Lee et al. | |
| 2001/0009976 A1 | 7/2001 | Panescu et al. | |
| 2001/0020166 A1 | 9/2001 | Daly et al. | |
| 2001/0029366 A1 | 10/2001 | Swanson et al. | |
| 2001/0037109 A1 * | 11/2001 | Yamauchi et al. | 606/48 |
| 2001/0039415 A1 * | 11/2001 | Francischelli et al. | 606/27 |
| 2001/0044625 A1 | 11/2001 | Hata et al. | |
| 2001/0051803 A1 | 12/2001 | Desai et al. | |
| 2002/0065465 A1 | 5/2002 | Panescu et al. | |
| 2002/0111548 A1 | 8/2002 | Swanson et al. | |
| 2002/0120263 A1 | 8/2002 | Brown et al. | |
| 2002/0126036 A1 * | 9/2002 | Flaherty et al. | 341/176 |
| 2002/0128643 A1 | 9/2002 | Sherman | |
| 2002/0143250 A1 | 10/2002 | Panescu et al. | |
| 2002/0161422 A1 | 10/2002 | Swanson et al. | |
| 2003/0018330 A1 | 1/2003 | Swanson et al. | |
| 2003/0055419 A1 | 3/2003 | Panescu et al. | |
| 2003/0055420 A1 | 3/2003 | Sherman | |
| 2003/0093069 A1 | 5/2003 | Panescu et al. | |
| 2003/0125730 A1 | 7/2003 | Berube et al. | |
| 2003/0181819 A1 | 9/2003 | Desai | |
| 2003/0195407 A1 | 10/2003 | Fuimaono et al. | |
| 2003/0195501 A1 | 10/2003 | Sherman et al. | |
| 2003/0199746 A1 | 10/2003 | Fuimaono et al. | |
| 2003/0204185 A1 | 10/2003 | Sherman | |
| 2003/0204186 A1 | 10/2003 | Geistert | |
| 2004/0015164 A1 | 1/2004 | Fuimaono et al. | |
| 2004/0082947 A1 | 4/2004 | Oral et al. | |
| 2004/0116921 A1 | 6/2004 | Sherman et al. | |
| 2004/0133154 A1 | 7/2004 | Flaherty et al. | |
| 2004/0138545 A1 | 7/2004 | Chen et al. | |
| 2004/0143256 A1 | 7/2004 | Bednarek | |
| 2004/0152980 A1 | 8/2004 | Desai | |
| 2004/0158141 A1 | 8/2004 | Scheib | |
| 2004/0181139 A1 | 9/2004 | Falwell et al. | |
| 2004/0181249 A1 * | 9/2004 | Torrance et al. | 606/170 |
| 2004/0182384 A1 | 9/2004 | Alfery | |
| 2004/0236324 A1 | 11/2004 | Muller et al. | |
| 2004/0247164 A1 * | 12/2004 | Furnish | 382/128 |
| 2005/0010095 A1 | 1/2005 | Stewart et al. | |
| 2005/0015084 A1 | 1/2005 | Hill et al. | |
| 2005/0033137 A1 | 2/2005 | Oral et al. | |
| 2005/0065512 A1 | 3/2005 | Schaer | |
| 2005/0096644 A1 | 5/2005 | Hall et al. | |
| 2005/0101946 A1 | 5/2005 | Govari et al. | |
| 2005/0119651 A1 | 6/2005 | Fuimaono et al. | |
| 2005/0148892 A1 | 7/2005 | Desai | |
| 2005/0177146 A1 | 8/2005 | Sherman | |
| 2005/0187545 A1 | 8/2005 | Hooven et al. | 606/41 |
| 2005/0234444 A1 | 10/2005 | Hooven | |
| 2005/0240176 A1 | 10/2005 | Oral et al. | |
| 2005/0251132 A1 | 11/2005 | Oral et al. | |
| 2005/0256521 A1 | 11/2005 | Kozel | |
| 2006/0030844 A1 | 2/2006 | Knight et al. | |
| 2006/0084966 A1 | 4/2006 | Maguire et al. | |
| 2006/0089637 A1 | 4/2006 | Sherman | |
| 2006/0095030 A1 | 5/2006 | Avitall et al. | |
| 2006/0106375 A1 * | 5/2006 | Werneth et al. | 606/32 |
| 2006/0111700 A1 | 5/2006 | Sherman | |
| 2006/0111701 A1 | 5/2006 | Oral et al. | |
| 2006/0111702 A1 | 5/2006 | Oral et al. | |
| 2006/0111703 A1 | 5/2006 | Kunis et al. | |
| 2006/0111708 A1 | 5/2006 | Vanney et al. | |
| 2006/0122526 A1 | 6/2006 | Berenfeld et al. | |
| 2006/0142753 A1 | 6/2006 | Francischelli et al. | |
| 2006/0189975 A1 | 8/2006 | Whayne et al. | |
| 2006/0195082 A1 | 8/2006 | Francischelli | |
| 2006/0206109 A1 | 9/2006 | Swanson | |
| 2006/0241366 A1 | 10/2006 | Falwell et al. | |
| 2007/0027448 A1 | 2/2007 | Paul et al. | |
| 2007/0049816 A1 | 3/2007 | Damiano et al. | |
| 2007/0083194 A1 | 4/2007 | Kunis et al. | |
| 2007/0083195 A1 * | 4/2007 | Werneth et al. | 606/41 |
| 2007/0106293 A1 | 5/2007 | Oral et al. | |

FOREIGN PATENT DOCUMENTS

| | | |
|---|---|---|
| CA | 2327518 | 11/1999 |
| CA | 2328064 | 11/1999 |
| CA | 2328070 | 11/1999 |
| CA | 2371935 | 12/2000 |
| CA | 2222617 C | 7/2002 |
| CA | 2437140 | 6/2004 |
| CA | 2492283 | 7/2005 |
| CA | 2194061 C | 4/2006 |
| CA | 2276755 C | 5/2006 |
| CA | 2251041 C | 6/2006 |
| EP | 428812 B1 | 3/1995 |
| EP | 779059 A | 6/1997 |
| EP | 0823843 B1 | 2/1998 |
| EP | 598742 B1 | 8/1999 |

(56) References Cited

FOREIGN PATENT DOCUMENTS

| | | |
|---|---|---|
| EP | 879016 B1 | 10/2003 |
| EP | 1360938 A1 | 11/2003 |
| EP | 1364677 A2 | 11/2003 |
| EP | 1554986 B1 | 7/2005 |
| EP | 1384445 B1 | 2/2006 |
| EP | 1169976 B1 | 4/2006 |
| EP | 1415680 B1 | 4/2006 |
| EP | 1011437 B1 | 5/2006 |
| EP | 1210021 B1 | 5/2006 |
| EP | 1658818 A1 | 5/2006 |
| EP | 1125549 B1 | 6/2006 |
| EP | 1182980 B1 | 6/2006 |
| EP | 1207798 B1 | 6/2006 |
| EP | 1321166 B1 | 7/2006 |
| EP | 1343427 B1 | 7/2006 |
| EP | 1690564 A1 | 8/2006 |
| EP | 828451 B1 | 9/2006 |
| EP | 1070480 B1 | 9/2006 |
| EP | 1014874 B1 | 12/2006 |
| EP | 1383437 B1 | 12/2006 |
| EP | 1455667 B1 | 1/2007 |
| EP | 1750215 A1 | 2/2007 |
| EP | 957794 B1 | 7/2007 |
| JP | 2004188179 A | 7/2004 |
| SU | 1512622 A1 | 10/1989 |
| SU | 1544396 A1 | 2/1990 |
| SU | 1690786 A1 | 11/1991 |
| WO | WO90/06079 A1 | 6/1990 |
| WO | WO93/08756 A1 | 5/1993 |
| WO | WO 93/25273 | 12/1993 |
| WO | WO94/12098 A1 | 6/1994 |
| WO | WO96/10961 A1 | 4/1996 |
| WO | WO96/32885 A1 | 10/1996 |
| WO | WO96/32897 A1 | 10/1996 |
| WO | WO 96/34558 | 11/1996 |
| WO | WO96/34559 A1 | 11/1996 |
| WO | WO96/34560 A1 | 11/1996 |
| WO | WO96/34567 A1 | 11/1996 |
| WO | WO 96/34569 | 11/1996 |
| WO | WO96/34570 A1 | 11/1996 |
| WO | WO96/34650 A1 | 11/1996 |
| WO | WO96/34652 A1 | 11/1996 |
| WO | WO96/34653 A1 | 11/1996 |
| WO | WO 96/36860 | 11/1996 |
| WO | WO 96/39967 | 12/1996 |
| WO | WO97/15919 A1 | 5/1997 |
| WO | WO 97/17893 | 5/1997 |
| WO | WO97/17904 A1 | 5/1997 |
| WO | WO97/25917 A1 | 7/1997 |
| WO | WO97/25919 A1 | 7/1997 |
| WO | WO97/32525 A1 | 9/1997 |
| WO | WO97/36541 A1 | 10/1997 |
| WO | WO97/40760 A1 | 11/1997 |
| WO | WO97/42996 A1 | 11/1997 |
| WO | WO98/18520 A2 | 5/1998 |
| WO | WO98/19611 A1 | 5/1998 |
| WO | WO98/26724 A1 | 6/1998 |
| WO | WO 98/28039 | 7/1998 |
| WO | WO 98/38913 | 9/1998 |
| WO | WO99/02096 A1 | 1/1999 |
| WO | WO99/56644 A1 | 11/1999 |
| WO | WO99/56647 A1 | 11/1999 |
| WO | WO99/56648 A1 | 11/1999 |
| WO | WO99/56649 A1 | 11/1999 |
| WO | WO00/78239 A2 | 12/2000 |
| WO | WO02/060523 A2 | 8/2002 |
| WO | WO03/041602 A2 | 5/2003 |
| WO | WO 03/089997 | 10/2003 |
| WO | WO 2005/027765 | 3/2005 |
| WO | WO 2005/027766 | 3/2005 |
| WO | WO2005/065562 A1 | 7/2005 |
| WO | WO2005/065563 A1 | 7/2005 |
| WO | WO2005/104972 A2 | 11/2005 |
| WO | WO 2006/017517 | 2/2006 |
| WO | WO 2006/044794 | 4/2006 |
| WO | WO2006/049970 A2 | 5/2006 |
| WO | WO2006/052651 A1 | 5/2006 |
| WO | WO2006/052905 A2 | 5/2006 |
| WO | WO 2006/055654 | 5/2006 |
| WO | WO 2006/055658 | 5/2006 |
| WO | WO 2006/055733 | 5/2006 |
| WO | WO 2006/055741 | 5/2006 |
| WO | WO2007/001981 A2 | 1/2007 |
| WO | WO2007/016123 A2 | 2/2007 |
| WO | WO2007/024785 A2 | 3/2007 |
| WO | WO2007/024983 A2 | 3/2007 |

OTHER PUBLICATIONS

Oral et al., "Segmental ostial ablation to isolate the pulmonary veins during atrial fibrillation: feasibility and mechanistic insights," Circulation, vol. 106, pp. 1256-1262, 2002.

Nademanee et al., "A new approach for catheter ablation of atrial fibrillation: mapping of the electrophysiologic substrate," JACC, vol. 43, No. 11, pp. 2044-2053, 2004.

Wittkampf et al., "Radiofrequency ablation with a cooled porous electrode catheter," (abstract) JACC, vol. 11, No. 2, pp. 17a, Feb. 1988.

Oral et al.; U.S. Appl. No. 11/932,378 entitled "Ablation catheters and methods for their use," filed Oct. 31, 2007.

Werneth et al.; U.S. Appl. No. 12/116,753 entitled "Ablation therapy system and method for treating continuous atrial fibrillation," filed May 7, 2008.

Sherman et al.; U.S. Appl. No. 12/117,596 entitled RF energy delivery system and method, filed May 8, 2008.

Oral et al.; U.S. Appl. No. 12/176,115 entitled "Atrial ablation catheter adapted for treatment of septal wall arrhythmogenic foci and method of use," filed Jul. 18, 2008.

Kunis et al.; U.S. Appl. No. 12/197,425 entitled "Atrial ablation catheter and method of use," filed Aug. 25, 2008.

Werneth et al.; U.S. Appl. No. 12/245,625 entitled "Ablation catheter," filed Oct. 3, 2008.

* cited by examiner

USER INTERFACE FOR TISSUE ABLATION SYSTEM

CROSS-REFERENCE TO RELATED APPLICATIONS

This application claims the benefit of U.S. Provisional Patent Application Ser. No. 60/710,451, filed Aug. 22, 2005, entitled "User Interface For Tissue Ablation System," which is incorporated by reference herein in its entirety.

FIELD OF THE INVENTION

The present invention relates generally to systems, catheters and methods for performing targeted tissue ablation in a subject. In particular, the present invention provides catheters comprising two or more ablation elements configured to precisely and efficiently deliver energy to tissue, and a sophisticated user interface that allows simplified use of the multi ablation element catheters.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. Often the ablation is performed by passing energy, such as electrical energy, through one or more electrodes causing the tissue in contact with the electrodes to heat up to an ablative temperature. Ablation procedures can be performed on patients with atrial fibrillation by ablating tissue in the heart.

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This condition overwhelms the atrioventricular node into producing an irregular and rapid heartbeat. As a result, blood pools in the atria and increases the risk of blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are limited. Three known treatments, lifestyle change, medical therapy and electrical cardioversion all have significant limitations. Lifestyle change only assists individuals with lifestyle-related atrial fibrillation. Medication therapy assists only in the management of atrial fibrillation symptoms, may present side effects more dangerous than atrial fibrillation, and fail to cure atrial fibrillation. Electrical cardioversion attempts to restore sinus rhythm but has a high recurrence rate. In addition, if there is a blood clot in the atria, cardioversion may cause the clot to leave the heart and travel to the brain or to some other part of the body, which may lead to stroke. What are needed are new methods for treating atrial fibrillation and other conditions involving disorganized electrical conduction.

Various ablation techniques have been proposed to treat atrial fibrillation, including the Cox-Maze procedure, linear ablation of various regions of the atrium, and circumferential ablation of pulmonary vein ostia. The Cox-Maze procedure and linear ablation procedures are unrefined, unnecessarily complex, and imprecise, with unpredictable and inconsistent results and an unacceptable level of unsuccessful procedures. These procedures are also tedious and time-consuming, taking several hours to accomplish. Pulmonary vein ostial ablation is proving to be less effective and when ablations are performed too close or inside the pulmonary vein rapid stenosis and potential occlusion of the pulmonary veins can result. There is therefore a need for improved atrial ablation catheters, systems and techniques, as well as sophisticated user interfaces to safely and effectively use these catheters.

BRIEF SUMMARY OF THE INVENTION

According to a first aspect of the invention, an ablation system used by an operator to treat a patient is disclosed. The system comprises a ablation catheters that have a flexible carrier assembly that includes at least two ablation elements configured to map electrocardiogram and deliver energy to tissue. The system further includes an interface unit for providing energy to the ablation elements of the ablation catheter. The interface unit also has a visual display that provides to the operator a visual representation of the geometry of the at least two ablation elements. Information such as system parameter information is displayed in geometric relation to the visual representation of the ablation elements enabling simplified viewing and modifying of system parameters.

According to a second aspect of the invention, an ablation system used by an operator to treat a patient is disclosed. The system comprises an ablation catheter that has a flexible carrier assembly that includes at least two ablation elements configured to deliver energy to tissue. The system further includes an interface unit for providing energy to the ablation elements of the ablation catheter. The interface unit also has a control interface with a visual display. The control interface includes selection means configured to permit an operator to select an icon displayed on the visual display. Selection of the icon is used to modify the form in which information is displayed, or select information to be modified.

According to a third aspect of the invention, a percutaneous catheter for performing a sterile medical procedure is disclosed. The catheter is for inserting into a body cavity such as a vessel of a patient and includes an elongate tubular structure with a proximal end and a distal end. On the proximal end of the tubular structure is a handle that is maintained within a sterile field during the medical procedure. The handle further includes a control assembly for controlling a separate medical device. In a preferred embodiment, the separate medical device is outside of the sterile field.

BRIEF DESCRIPTION OF THE SEVERAL VIEWS OF THE DRAWINGS

The accompanying drawings, which are incorporated in and constitute a part of this specification, illustrate various embodiments of the present invention, and, together with the description, serve to explain the principles of the invention. In the drawings:

FIG. 2b is a sectional view of a finned electrode of FIG. 2a.

FIG. 3b is a sectional view of a distal portion of the ablation catheter of FIG. 3a.

DETAILED DESCRIPTION OF THE INVENTION

Figure 1:
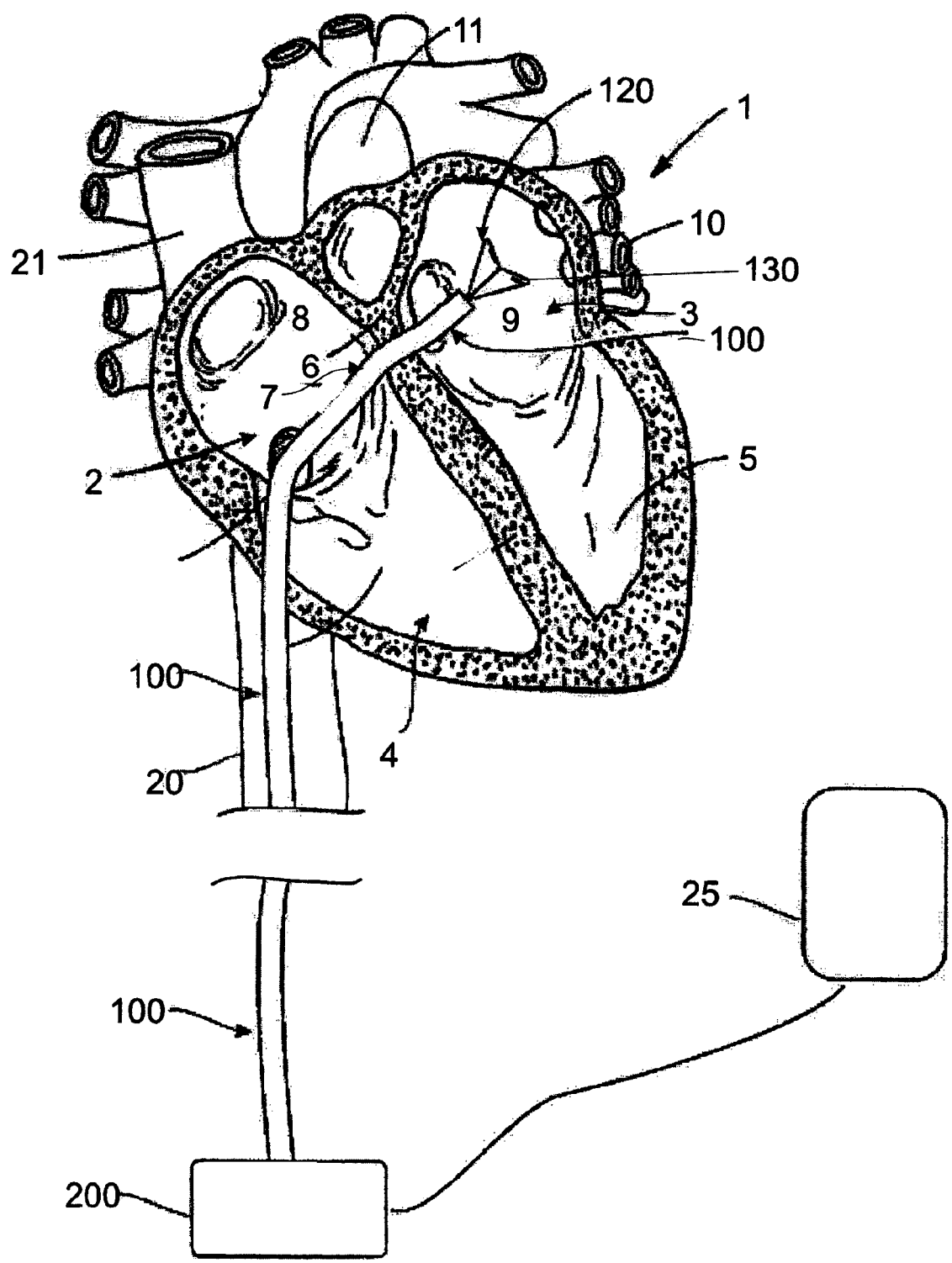
FIG. 1 illustrates the treatment to be accomplished with the devices and methods described below.

Reference will now be made in detail to the present embodiments of the invention, examples of which are illustrated in the accompanying drawings. Wherever possible, the same reference numbers will be used throughout the drawings to refer to the same or like parts.

The present invention utilizes ablation therapy. Tissue ablation is often used in treating several medical conditions, including abnormal heart rhythms. Ablation can be performed both surgically and non-surgically. Non-surgical ablation is typically performed in a special lab called the electrophysiology (EP) laboratory. During this non-surgical procedure a catheter is inserted into a vessel such as a vein, and guided into the heart using fluoroscopy for visualization. Subsequently, an energy delivery apparatus is used to supply energy to the heart muscle. This energy either "disconnects" or "isolates" the pathway of the abnormal rhythm. It can also be used to disconnect the conductive pathway between the upper chambers (atria) and the lower chambers (ventricles) of the heart. For individuals requiring heart surgery, ablation can be performed during coronary artery bypass or valve surgery.

The present invention provides catheters for performing targeted tissue ablation in a subject. In preferred embodiments, the catheters comprise a tubular body member having a proximal end and distal end and preferably a lumen extending therebetween. The catheter is preferably of the type used for performing intracardiac procedures, typically being introduced from the femoral vein in a patient's leg or a vein in the patient's neck. The catheter is preferably introducible through a sheath with a steerable tip that allows positioning of the distal portion to be used, for example, when the distal end of the catheter is within a heart chamber. The catheters include ablation elements mounted on a carrier assembly. The carrier assembly is preferably attached to a coupler, which in turn is connected to a control shaft that is coaxially disposed and slidingly received within the lumen of the tubular body member. The carrier assembly is deployable from the distal end of the tubular body member by advancing the control shaft, such as to engage one or more ablation elements against cardiac tissue, which is typically atrial wall tissue or other endocardial tissue. Retraction of the control shaft causes the carrier assembly to be constrained within the lumen of the tubular body member.

Arrays of ablation elements, preferably electrode arrays, may be configured in a wide variety of ways and patterns. In particular, the present invention provides devices with electrode arrays that provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like) with these devices. Alternative to or in combination with ablation elements that deliver electrical energy to tissue, other forms and types of energy can be delivered including but not limited to: sound energy such as acoustic energy and ultrasound energy; electromagnetic energy such as electrical, magnetic, microwave and radiofrequency energies; thermal energy such as heat and cryogenic energies; chemical energy such as energy generated by delivery of a drug; light energy such as infrared and visible light energies; mechanical and physical energy such as pressurized fluid; radiation; and combinations thereof.

As described above, the normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters of the present invention may be employed.

One current method of treating cardiac arrhythmias is with catheter ablation therapy, which, to date, has been difficult and impractical to employ. In catheter ablation therapy, physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician such as an electrophysiologist) directs a catheter through a main vein or artery into the interior region of the heart that is to be treated. The ablating element is next placed near the targeted cardiac tissue that is to be ablated. The physician directs energy, provided by a source external to the patient, from one ore more ablation elements to ablate the neighboring tissue and form a lesion. In general, the goal of catheter ablation therapy is to disrupt the electrical pathways in cardiac tissue to stop the emission of and/or prevent the propagation of erratic electric impulses, thereby curing the heart of the disorder. For treatment of atrial fibrillation, currently available methods and devices have shown only limited success and/or employ devices that are extremely difficult to use or otherwise impractical.

The ablation catheters of the present invention allow the generation of lesions of appropriate size and shape to treat conditions involving disorganized electrical conduction (e.g., atrial fibrillation). The ablation catheters and the energy-providing interface unit of the present invention are also practical in terms of ease-of-use and limiting risk to the patient, such as by significantly reducing procedure times. The present invention accomplishes these goals by, for example, the use of spiral shaped, radial arm shaped (also called umbrella shaped) and zigzag shaped carrier assemblies whose ablation elements create spiral, radial, zigzag or other simple or complex shaped patterns of lesions in the endocardial surface of the atria by delivery of energy to tissue or other means. The lesions created by the ablation catheters are suitable for inhibiting the propagation of inappropriate electrical impulses in the heart for prevention of reentrant arrhythmias. Simplified ease of use of these ablation catheters is accomplished with a sophisticated user interface, integral to the interface unit, which includes a visual display that provides a visual representation of the geometry of the ablation elements of the ablation catheter.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited to, individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures.

As used herein, the term "ablation element" refers to an energy delivery element, such as an electrode for delivering electrical energy. Ablation elements can be configured to deliver multiple types of energy, such as ultrasound energy and cryogenic energy, either simultaneously or serially. Electrodes can be constructed of a conductive plate, wire coil, or other means of conducting electrical energy through contacting tissue. In monopolar energy delivery, the energy is conducted from the electrode, through the tissue to a ground pad, such as a conductive pad attached to the back of the patient. The high concentration of energy at the electrode site causes localized tissue ablation. In bipolar energy delivery, the energy is conducted from a first electrode to one or more separate electrodes, relatively local to the first electrode, through the tissue between the associated electrodes. Bipolar energy delivery results in more precise, shallow lesions while monopolar delivery results in deeper lesions. Both monopolar and bipolar delivery provide advantages, and the combination of their use is a preferred embodiment of this application. Energy can also be delivered using pulse width modulated drive signals, well known to those of skill in the art. Energy can also be delivered in a closed loop fashion, such as a system with temperature feedback wherein the temperature modifies the type, frequency and/or magnitude of the energy delivered.

As used herein, the term "carrier assembly" refers to a flexible carrier, on which one or more ablation elements are disposed. Carrier assemblies are not limited to any particular size, or shape, and can be configured to be constrained within an appropriately sized lumen.

As used herein, the term "spiral tip" refers to a carrier assembly configured in its fully expanded state into the shape of a spiral. The spiral tip is not limited in the number of spirals it may contain. Examples include, but are not limited to, a wire tip body with one spiral, two spirals, ten spirals, and a half of a spiral. The spirals can lie in a relatively single plane, or in multiple planes. A spiral tip may be configured for energy delivery during an ablation procedure.

As used herein the term "umbrella tip" refers to a carrier assembly with a geometric center which lies at a point along the axis of the distal portion of the tubular body member, with one or more bendable or hinged carrier arms extending from the geometric center, in an umbrella configuration. Each carrier arm may include one or more ablation elements. Each carrier arm of an umbrella tip includes a proximal arm segment and a distal arm segment, the distal arm segment more distal than the proximal arm segment when the carrier assembly is in a fully expanded condition. One or more additional carrier arms can be included which include no ablation elements, such as carrier arms used to provide support or cause a particular deflection. An umbrella tip body is not limited to any particular size. An umbrella tip may be configured for energy delivery during an ablation procedure.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein, the term "spiral lesion" refers to an ablation lesion delivered through a spiral tip ablation catheter. Examples include, but are not limited to, lesions in the shape of a wide spiral, and a narrow spiral, a continuous spiral and a discontinuous spiral.

As used herein, the term "umbrella lesion" or "radial lesion," and like terms, refers to an ablation lesion delivered through an umbrella tip ablation catheter. Examples include, but are not limited to, lesions with five equilateral prongs extending from center point, lesions with four equilateral prongs extending from center point, lesions with three equilateral prongs extending from center point, and lesions with three to five non-equilateral prongs extending from center point.

As used herein, the term "coupler" refers to an element that connects the carrier assembly to the control shaft. Multiple shafts, or ends of the carrier assembly may connect to the coupler. Multiple carrier arms can have one or more of their ends attached to the coupler. The coupler may include anti-rotation means that work in combination with mating means in the tubular body member. Couplers may be constructed of one or more materials such as polyurethane, steel, titanium, and polyethylene.

As used herein, the term "carrier arm" refers to a wire-like shaft capable of interfacing with electrodes and the coupler. A carrier arm is not limited to any size or measurement. Examples include, but are not limited to: stainless steel shafts; Nitinol shafts; titanium shafts; polyurethane shafts; nylon shafts; and steel shafts. Carrier arms can be entirely flexible, or may include flexible and rigid segments.

As used herein, the term "carrier arm bend point" refers to a joint (e.g., junction, flexion point) located on a carrier arm. The degree of flexion for a carrier arm bend point may range from 0 to 360 degrees. The bend portion can be manufactured such that when the carrier assembly is fully expanded, the bend point is positioned in a relatively straight configuration, a curved configuration, or in a discrete transition from a first direction to a second direction, such as a 45 degree bend transition. The bend portion can include one or more flexing means such as a spring, a reduced diameter segment, or a segment of increased flexibility.

The present invention provides structures that embody aspects of the ablation catheter. The present invention also provides tissue ablation systems and methods for using such ablation systems. The illustrated and various embodiments of the present invention present these structures and techniques in the context of catheter-based cardiac ablation. These structures, systems, and techniques are well suited for use in the field of cardiac ablation.

However, it should be appreciated that the present invention is also applicable for use in other tissue ablation applications such as tumor ablation procedures. For example, the various aspects of the invention have application in procedures for ablating tissue in the prostrate, brain, gall bladder, uterus, and other regions of the body, preferably regions with an accessible wall or flat tissue surface, using systems that are not necessarily catheter-based.

The multifunctional catheters of the present invention have numerous advantages over previous prior art devices. The present invention achieves efficiency in tissue ablation by maximizing contact between electrodes and tissue, such as the atrial walls, while also achieving rapid and/or efficient transfer of heat from the electrode into the circulating blood ("cooling"), such as by maximizing electrode surface area in contact with circulating blood. To achieve this result, in a preferred embodiment the electrode has a projecting fin that is configured to act as a heat sink that provides rapid and efficient cooling of the electrode. In another preferred embodiment the electrode comprises two components such that one component, the electrode conductive portion, contracts tissue and the other component, the nonconductive portion, remains thermally conductive. The present invention includes electrodes with improved and miniaturized cross sectional geometries and carrier assemblies that "fold-up" efficiently to allow a smaller ablation catheter to be employed. These improved electrodes are preferably triangularly shaped as described in detail in reference to subsequent figures below. Because these triangular electrodes fold up efficiently, and can have either a "base" to contact tissue or a "point" to contact tissue, greater efficiency and versatility are achieved. The devices and systems are configured to minimize the amount of tissue ablated while still achieving the desired therapeutic benefit of the ablation therapy. Ablated lesions are created with a target depth, and minimal widths. System components monitor energy delivered, parameters associated with energy delivered and other system parameters. Energy delivered is prevented from achieving one or more threshold values.

FIGS. 1-7 show various embodiments of the multifunctional catheters of the present invention. The present invention is not limited to these particular configurations.

FIG. 1 illustrates the treatment to be accomplished with the devices and methods described herebelow. FIG. 1 shows a cutaway view of the human heart 1 showing the major structures of the heart including the right atrium 2, the left atrium 3, the right ventricle 4, and the left ventricle 5. The atrial septum 6 separates the left and right atria. The fossa ovalis 7 is a small depression in the atrial septum that may be used as an access pathway to the left atrium from the right atrium. The fossa ovalis 7 can be punctured, and easily reseals and heals after procedure completion. In a patient suffering from atrial fibrillation, aberrant electrically conducive tissue may be found in the atrial walls 8 and 9, as well as in the pulmonary veins 10 and the pulmonary arteries 11. Ablation of these areas, referred to arrhythmogenic foci (also referred to as drivers or rotors), is an effective treatment for atrial fibrillation. Though circumferential ablation of the pulmonary vein usually cures the arrhythmia that originates in the pulmonary veins, as a sole therapy it is usually associated with lesions that have high risk of the eventual stenosis of these pulmonary veins, a very undesirable condition. The catheters of the present invention provide means of creating lesions remote from these pulmonary veins and their ostia while easily being deployed to ablate the driver and rotor tissue.

To accomplish this, catheter 100 is inserted into the right atrium 2, preferably through the inferior vena cava 20, as shown in the illustration, or through the superior vena cava 21. Catheter 100 may include an integral sheath, such as a tip deflecting sheath, or may work in combination with a separate sheath. When passing into the left atrium, the catheter passes through or penetrates the fossa ovalis 7, such as over a guide wire placed by a trans-septal puncture device. The catheter 100 carries a structure carrying multiple ablation elements such as RF electrodes, carrier assembly 120, into the left atrium. Carrier assembly 120, which includes multiple electrodes 130, can be advanced and retracted out of distal end of catheter 100. Carrier assembly 120 is adapted to be deformable such that pressing carrier assembly 120 into left atrial wall 9 will cause one or more, and preferably all of electrodes 130 to make contact with tissue to be analyzed and/or ablated. Each of the electrodes 130 is attached via connecting wires to an energy delivery apparatus, RF delivery unit 200, which is also attached to patch electrode 25, preferably a conductive pad attached to the back of the patient.

RF delivery unit 200 is configured to deliver RF energy in monopolar, bipolar or combination monopolar-bipolar energy delivery modes. In a preferred embodiment, monopolar energy delivery is followed by bipolar energy delivery. In an alternative embodiment, the bipolar energy is then followed by a period without energy delivery; such as a sequence in which the three steps are have equal durations. In another preferred embodiment, RF delivery unit 200 is configured to also provide electrical mapping of the tissue that is contacted by one or more electrodes integral to carrier assembly 120. Electrodes 130, preferably with a triangular cross section, can also be configured to be mapping electrodes and/or additional electrodes can be integral to carrier assembly 120 to provide a mapping function. Carrier assembly 120 is engagable over an endocardial surface to map and/or ablate tissue on the surface. RF energy is delivered after a proper location of the electrodes 130 is confirmed with a mapping procedure. If the position is determined to be inadequate, carrier assembly 120 is repositioned through various manipulations at the proximal end of the ablation catheter 100. In another preferred embodiment, RF delivery unit 200 is configured to deliver both RF energy and ultrasound energy through identical or different electrodes 130. In another preferred embodiment, RF delivery unit 200 is configured to accept a signal from one or more sensors integral to ablation catheter 100, not shown, such that the energy delivered can be modified via an algorithm which processes the information received from the one or more sensors. The improved electrodes and other catheter and system components of the present invention typically require only 3 to 5 watts of RF energy to adequately ablate the tissue. The minimal power requirements results in reduced procedure time as well as greatly enhanced safety of the overall procedure.

Figure 2A:
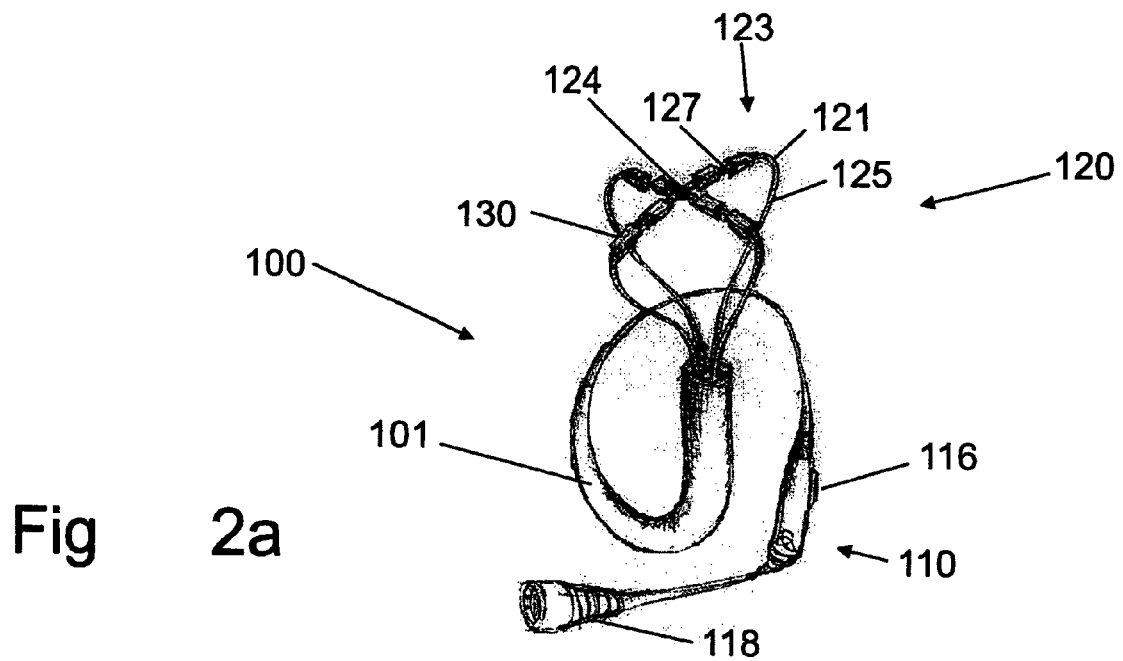
FIG. 2a illustrates a perspective view of an ablation catheter consistent with the present invention in which the carrier element has four carrier arms each including two ablation elements.
Figure 2B:
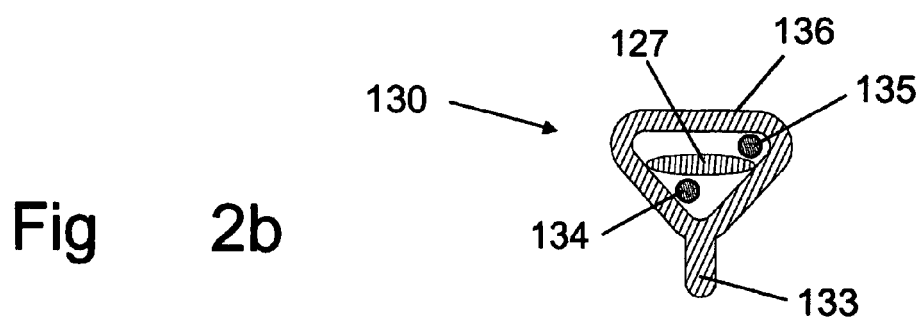

FIGS. 2a and 2b illustrate an exemplary embodiment of the ablation catheter 100 of the present invention. These ablation catheters have triangular electrodes 130, each with fin 133 configured to provide rapid and efficient cooling of electrode 130. The cooling efficiency prevents over-heating of the electrode and neighboring tissue during ablation, as well as a short transition time from an ablation temperature, preferably 60° C., to body temperature, typically 37° C. after an ablation cycle has ceased. This rapid transition is typically less than 20 seconds, even when the electrode remains in contact with recently ablated tissue. Other benefits of the rapid and efficient cooling electrode configuration include reducing the risk of blood clotting.

The ablation elements of the present invention include RF energy delivery electrodes 130 of FIGS. 2a and 2b, as well as other elements capable of delivering one or more forms of energy, described in detail hereabove, the electrodes and other system components configured in a manner sufficient to controllably ablate tissue. Electrodes 130 include conductive materials, such as a metal or metal-coated material. Metals and combinations of metals are appropriate such as: platinum, iridium, gold, stainless steel and aluminum. Conductive polymers are also appropriate materials. Conductive surfaces may be painted, coated or plated surfaces, such as gold plated over a copper base. Electrode materials may also include foils such as aluminum or gold foils attached to a base. Electrodes 130 deliver RF energy in monopolar or bipolar mode as has been described in reference to FIG. 1. Electrodes 130 are designed to have small surface area, typically less than 2.5 mm$^2$ and preferably approximating 0.56 mm$^2$. Electrodes 130 are designed to have small volume, typically less than 3.0 mm$^3$ and preferably approximating 1.3 mm$^3$. Electrodes 130 are designed to have small mass, typically less than 0.05 grams, and preferably approximating 0.03 grams. These miniaturized electrodes, especially those with a triangular cross section, provide numerous advantages such as high ratio of energy to surface area (energy density) during ablation, as well as efficiently compact volume of carrier assembly 120 when constrained within the lumen of the ablation catheter in the retracted, undeployed state.

FIG. 2a shows the structures of the ablation carrier assembly 120 and other portions of ablation catheter 100. The ablation carrier assembly 120 shown includes carrier arms 123 that extend radially out from the central axis of the distal end of catheter shaft 101, the carrier arms 123 positioned in a symmetric configuration with equal angles (ninety degrees in a four arm configuration between each arm). Carrier assembly 120 is shown with four carrier arms 123, however any number can be used, and each arm can carry one or more mapping or ablating electrodes 130, or be void of electrodes. Carrier arms 123 are resiliently biased, preferably constructed of a wire such as a ribbon wire, and may have segments with different levels of flexibility. Carrier arms 123 are shown with multiple electrodes 130 fixedly mounted (such as with glues, soldering, welding, crimping or other attachment means) to its distal arm segment 127. In an alternative embodiment, different patterns of electrodes are employed, and one or more arms may be void of electrodes such as where carrier arm 123 provides support only. In a preferred embodiment, different types of ablation elements are mounted to one or more carrier arms 123, such as electrodes with different geometries, or ablation elements that deliver different forms of energy. Carrier arms 123 may also include mapping electrodes, thermal sensors or other sensors, with or without the inclusion of ablation elements. In a preferred embodiment, each carrier arm 123 includes at least one ablation element. In alternative embodiments, three or more arms can be separated by non-equal angles.

Each carrier arm 123 includes proximal arm segment 125 and distal arm segment 127. Electrodes 130 are mounted onto distal arm segment 127. During the ablation procedure, an operator presses distal arm segment 127 into tissue prior to and during energy delivery. Carrier assembly 120 is configured with specific rigidity such that the operator can exert a nominal force to cause the appropriate electrodes 130 to press and slightly "bury" into the tissue, without perforating or otherwise damaging the neighboring tissue. In a preferred embodiment, the distal arm segments contain thermocouples such as sensors embedded in the electrodes 130, or sensors mounted equidistant between two electrodes 130. Proximal arm segment 125 and distal arm segment 127 connect at a bendable joint, carrier arm bend point 121. In a preferred embodiment, proximal arm segment 125, distal arm segment 127 and bend point 121 are a continuous resiliently flexible wire. Each distal arm segment 127 bends radially inward from the bend point 121 toward the longitudinal axis of catheter shaft 101. The distal arm segments 127 are shown also to tend proximally, to establish an acute angle with the proximal arm segment 125 from which it extends, and the angle is small such that the distal end of the distal arm segment 127 is proximal to the carrier arm bend point 121. Bend point 121 allows "folding out" of carrier assembly 120 during retraction, acting as a hinge in providing the means for rotably joining the distal arm segment 127 to the proximal arm segment 125. The proximal arm segment 125 of the carrier arm 123 may include temperature sensors, not shown, such as thermocouples to measure temperature of blood. In the configuration shown, the proximal arm segment 125 will not contact tissue during the ablation procedure. In an alternative embodiment, proximal arm segment 125 includes one or more electrodes, for ablation and/or for mapping, such that the opposite side of carrier assembly 120 can be used to map or ablate tissue and is configured to contact tissue, such as when carrier assembly 120 is deployed and catheter shaft 101 is in tension such as when pulled back by an operator.

Each distal arm segment 127 connects, at its end opposite bend point 121, to connection point 124, a mechanical joint such as a soldered, crimped or welded connection that stabilizes each distal arm segment 127 relative to the others. In a preferred embodiment, two continuous wires or ribbons are used to create the four distal arm segments 127. Each wire or ribbon comprises the pair of distal arm segments 127 that are linearly aligned, and the two wires are connected at their midpoint at connection point 124. These wires or ribbons are preferably constructed of Nitinol, but other materials such as stainless steel or a plastic may be used. In an alternative embodiment, the two connection wires are resiliently biased to deploy in the configuration shown in FIG. 2a, but do not include connection point 124 such that the center portion of the two continuous wires can move relative to each other.

Referring to the ablation catheter 100 structures, FIG. 2a shows a tubular body member that is an elongated, flexible, hollow tube, catheter shaft 101, which connects at its proximal end to handle 110. The material used for the construction of the catheter shaft 101 and each component which resides or is configured to be inserted through a lumen integral to catheter shaft 101, are selected to provide the suitable flexibility, column strength and steerability to allow percutaneous introduction of ablation catheter 100 through the vasculature of the patient, entering the right atrium 2 through the septum 6 and into the left atrium 3. Catheter shaft 101 and other tubular conduits of ablation catheter 100 are constructed of materials such as Pebax, urethanes, nylons, thermoplastic elastomers, and polyimides. The shafts may be reinforced with wire or plastic braids and/or may include coil springs. Catheter shaft 101 is typically between 4 to 12 French and typically 6 to 8 French. In a preferred embodiment, catheter shaft 101 is introduced through a deflectable sheath where the sheath mechanism is already in place in left atrium 3. In an alternative embodiment, catheter 100 is inserted directly without the use of an outer sheath, and catheter 100 includes a deflectable tip assembly and deflection controls.

Handle 110 on the ablation catheter includes controls to operate the carrier assembly 120. Handle 110 is constructed of a rigid or semi-rigid material such as Delrin or polycarbonate, and includes button 116 that is connected to switch means, not shown, for starting and/or stopping the delivery of energy to one or more of electrodes 130. Handle 110 may include other controls, not shown, to perform numerous functions such as change energy delivery settings. Handle 110 may include a retraction mechanism, not shown, to advance and retreat carrier assembly 120. In an alternative embodiment, handle 110 is attached to an inner shaft slidingly received within catheter shaft 101 such that retraction of the handle 110 causes the carrier assembly 120 to collapse and be constrained within the lumen at end of catheter shaft 101. Carrier arm 123 is resiliently biased in shown position so that it can be collapsed and withdrawn within lumen of catheter shaft 101 through manipulation of handle 110 on proximal end of catheter 100.

Handle 110 includes a plug 118 that attaches to an interface unit of the present invention, such as an RF energy generator that also includes mapping functions and display. Plug 118 is connected to electrical wires that extend distally with a lumen integral to catheter shaft 101 of carrier assembly 120, terminating at each of the electrodes 130.

FIG. 2b illustrates the cross section, preferably a uniform cross section, of one or more electrodes 130 mounted to distal arm segment 127 of FIG. 2a. A projecting member, fin 133, assists in the rapid and efficient cooling of electrode 130 during and after ablation energy application, acting as a heat sink and efficiently transferring heat energy to the neighboring blood, such as blood circulating in the left atrium 3 or the right atrium 2 depending upon where the carrier assembly 120 has been placed by the operator. The size, surface area and mass of fin 133 are chosen to effectively transfer the heat energy while allowing carrier assembly 120 to achieve a sufficiently compact configuration when constrained within the lumen of the ablation catheter. In a preferred embodiment, fin 133 is sized such that the portion of the surface area of electrode 130 that is in contact with circulating blood is at least 60%, and preferably 70% of the total surface area of electrode 130. Fin 133 may change laminar and/or other non-turbulent flows to turbulent flow, such that heat is more efficiently transmitted away from electrode 130. In an alternative embodiment, fin 133 may be electrically isolated from the remainder of electrode 130, such that fin 133 does not deliver energy to the circulating blood. In another alternative embodiment, electrode 130 may include multiple fins.

First wire 134 is an energy delivery conduit that connects to electrode 130 to transfer ablation energy and preferably to also send and/or receive signals to map the tissue of the heart. Second wire 135 depicts an exemplary wire that connects to electrode 130, and may act as the return wire to first wire 134, for return of ablation energy and/or mapping signals. Wire 134 and wire 135 are typically 30 awg wire including a 0.003" polyamide insulating outer jacket, each parameter chosen to carry sufficient ablation currents and prevent voltage breakdown between neighboring wires. The efficiency of the electrodes of the present invention, as well as the efficient configuration of the other components of the system, allow greatly reduced wire gauge and insulation thickness, correlating to smaller diameter and more flexible ablation catheters.

Surface 136 is the base of the electrode that is the part of the structure that contacts tissue during ablation. In a preferred embodiment, surface 136 is a small surface area so that energy delivered per square area is maximized. Fin 133 projects from the apex opposite surface 136, and provides sufficient surface area such that the majority of the surface area of electrode 130 resides in the circulating blood when surface 136 is in contact with tissue and energy is being delivered. Within the triangular cross section of electrode 130 passes each wire 134 and 135, as well as distal arm segment 127, to which electrode 130 is fixedly mounted.

Figure 3A:
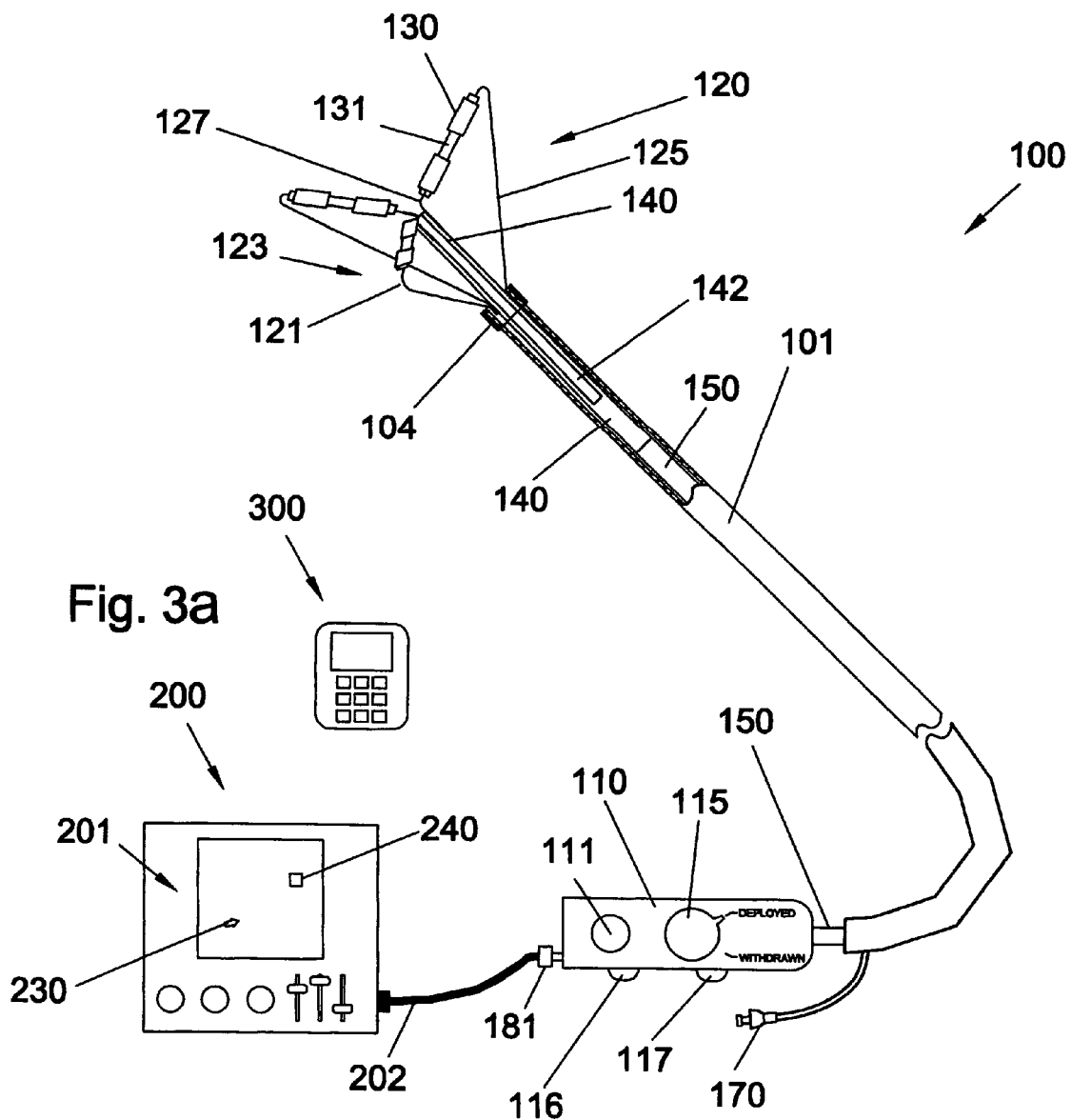
FIG. 3a illustrates a perspective, partial cutaway view of a preferred embodiment of an ablation catheter in which the carrier element has three carrier arms each including two ablation elements, an interface attached to the ablation catheter, and a remote control device, all consistent with the present invention.
Figure 3B:
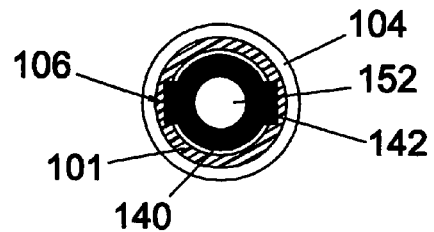

Referring now to FIGS. 3a and 3b, another preferred embodiment of an ablation catheter, system and method of the present invention is illustrated. The interface unit includes a control interface and means of selecting one or more icons of a visual display. The icons are selected to change information viewed or modify a parameter. Catheter 100 includes carrier assembly 120 configured in another umbrella tip configuration. Carrier assembly 120 includes three carrier arms 123, each separated by 120 degrees from the neighboring arm when in the deployed condition, and each of which includes two ablation elements, electrodes 130. In an alternative embodiment, different patterns of electrodes are employed, and one or more arms may be void of electrodes. Electrodes can take on one or more various forms, such as electrodes with energy delivery portions and non-energy delivery portions, electrodes with integral thermocouples, electrodes with projecting fins that provide a heat sinking function, and other types of electrodes. The six electrodes 130 shown may have similar or dissimilar characteristics. They may be chosen to maximize cooling or maximize energy delivery to tissue. Each electrode 130 may be energized with one or more forms of energy such as RF energy in a sequence of monopolar and bipolar energy delivery. In a preferred embodiment, multiple temperature sensors are integral to carrier assembly 130, temperature sensors not shown but preferably integral to electrodes 130 or fixedly attached to carrier arm 123 approximately mid-way between two electrodes 130. In another preferred embodiment, one or more force sensors are integral to carrier assembly 130, force sensors also not shown but typically one or more strain gauges integral to electrodes 130 or carrier arm 123. In a preferred embodiment, the strain gauge is mounted to an electrode 130 in a laminate construction, such that force exerted on the laminate assembly is indicative of the amount of contact of that electrode with tissue of the patient. Information from these types of sensors is carried by one or more wires, also not shown, to the interface unit of the present invention and provides system parameter information that can be displayed to one or more operators with current or historic values. This information can be compared to target values and/or threshold values to simplify and improve system performance.

Referring back to FIG. 3a, carrier arms 123 extend radially out from the central axis of the distal end of catheter shaft 101. Each carrier arm 123 includes proximal arm segment 125 and distal arm segment 127, these segments connected at a bendable joint, bend point 121. In a preferred embodiment, proximal arm segment 125 and distal arm segment 127 and bend point 121 are a continuous resiliently flexible wire, such as a "trained" Nitinol wire that creates the umbrella tip. Each electrode 130 is mounted to an insulator, insulating band 131 such that the electrode is electrically isolated from the wire segments of carrier assembly 120. Each electrode 130 is connected to wires that extend along shafts of carrier assembly 120, toward a lumen of catheter shaft 101, and proximally to handle 110. These wires, not shown but described in detail hereabove, include insulation to electrically isolate one wire from another. One end of each distal arm segment 127 is attached to a cylinder, coupler 140, which is sized to be slidably received within a lumen of catheter shaft 101.

Coupler 140 can be flexible or rigid, and may contain both rigid and flexible portions along its length. Coupler 140 may provide electrical connection means to connect wires extending from the handle to wires from carrier assembly 120 electrodes. The ends of the distal arm segments 127 and the ends of the proximal arm segments 125 can be attached to the outside of coupler 140, the inside of coupler 140 or both. Coupler 140 includes along its outer surface, a projection, projection 142, which has a cross section profile which mates with a recess, groove 106 of catheter shaft 101 which prevents undesired rotation of carrier assembly 120. In an alternative embodiment, catheter shaft 101 includes a projection, and coupler 140 includes a groove to accomplish a similar prevention of rotation. In another alternative embodiment, control shaft 150, which is slidingly received within a lumen of shaft 101, additionally or alternatively includes a projection or other means to mate with shaft 101 to prevent undesired rotation of carrier assembly 120. As depicted in FIG. 3*b*, control shaft 140 includes a thru lumen, lumen 152, such that ablation catheter 101 can be inserted over a guidewire (guidewire exit on handle 110 not shown). Additionally or alternatively, lumen 152 may include one or more wires or other filamentous conduits extending from proximal handle 110 a point more distal.

Control shaft 150 is mechanically attached to coupler 140. Control shaft 150 extends proximally to handle 110 and is operably connected to knob 115 such that rotation of knob 115 from a deployed position to a withdrawn position causes carrier assembly 120 to be constrained within a lumen of catheter shaft 101, and rotation of knob 115 from a withdrawn position to a deployed position causes carrier assembly 120 to extend beyond the distal end of catheter shaft 101 to be in an expanded condition. In a preferred embodiment, knob 115 is operably connected to control shaft 150 via a cam, or set of gears, not shown, to provide a mechanical advantage in the distance traveled by control shaft 150.

Catheter shaft 101 is preferably part of a steerable sheath, steering mechanism not shown, and includes flush port 170, which is configured to be attachable to a flushing syringe, used to flush blood and other debris or contaminants from the lumen of an empty catheter shaft 101 (wherein control shaft 150, coupler 140 and carrier assembly 120 have been removed) or for flushing the space between control shaft 150 and the inner wall of catheter shaft 101. Catheter shaft 101 is not connected to handle 110, such that handle 110 can be withdrawn, removing control shaft 150, coupler 140 and carrier assembly 120 from catheter shaft 101. This configuration is useful when these components are provided in a kit form, including combinations of different versions of these components, the different combinations made available to treat multiple patients, or a single patient requiring multiple electrode patterns or other varied electrode properties such as tissue contact surface area, electrode cooling properties and temperature sensor location. A preferred example of a kit would include the catheter shaft 101 and flush port 170 of FIG. 3*a* acting as a sheath; kitted with the insertable shaft assembly comprising handle 110, control shaft 150, coupler 140 and umbrella tipped carrier assembly 120 (also of FIG. 3*a*) combined with a second insertable shaft assembly. The second insertable shaft assembly preferably includes a differently configured carrier assembly such as an assembly with a different pattern of electrodes, or an assembly comprising electrodes with properties dissimilar from the electrodes of the first insertable shaft assembly. Electrode or other ablation element variations include but are not limited to: type of energy delivered; size; cross sectional geometry; cooling properties; heating properties; and combinations thereof. In another preferred embodiment of the kit, a catheter configured for creating lesions at or near the pulmonary veins of the left atrium is included.

Also depicted in FIG. 3*a* is a system of the present invention, including in addition to ablation catheter 100, RF delivery unit 200, an interface unit of the present invention which connects to handle 110 with a multi-conductor cable 202 at RF attachment port 181. RF delivery unit 200 includes user interface 201, such as a user interface including data input devices like touch screens, buttons, switches, keypads, magnetic readers and other input devices; and also including data output devices like data and image screens, lights, audible transducers, tactile transducers and other output devices. User interface 201 is used to perform numerous functions including but not limited to: selecting electrodes to receive energy (electrodes 130 of carrier assembly 120); setting power levels, types (bipolar and monopolar) and durations; setting catheter and other system threshold levels; setting mapping and other system parameters; initiating and ceasing power delivery; deactivating an alarm condition; and performing other functions common to electronic medical devices. User interface 201 also provides information to the operator including but not limited to: system parameter information including threshold information; mapping and ablation information including ablation element temperature and cooling information; and other data common to ablation therapy and other electronic medical devices and procedures. In a preferred embodiment, RF delivery unit 200 attaches to a temperature probe, such as an esophageal temperature probe, determines the temperature from one or more sensors integral to the probe, and further interprets and/or displays the temperature information on user interface 201. In another preferred embodiment, RF delivery unit 200 also includes cardiac mapping means, such that mapping attachment port 182 can be attached to RF delivery unit 200 avoiding the need for a separate piece of equipment in the system. In another preferred embodiment, RF delivery unit 200 can also deliver ultrasound and/or another form of energy, such energy delivered by one or more additional ablation elements integral to carrier assembly 120, additional ablation elements not shown. Applicable types of energy include but are not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical and physical energy such as pressurized fluid; radiation; and combinations thereof.

In a preferred embodiment, ablation catheter 100 includes an embedded identifier (ID), an uploadable electronic or other code, which can be used by RF delivery unit 200 to confirm compatibility and other acceptability of the specific catheter 100 with the specific RF delivery unit 200. The electronic code can be a bar code, not shown, on handle 110 which is read by RF delivery unit 200, an electronic code which is transferred to RF delivery unit 200 via a wired or wireless connection, not shown, or other identifying means, such as an RF tag embedded in handle 110. In another preferred embodiment, RF delivery unit 200 also includes an embedded ID, such as an ID that can be downloaded to catheter 100 for a second or alternative acceptability check. The embedded ID can also be used to automatically set certain parameters or certain parameter ranges, and can be used to increase safety by preventing inadvertent settings outside of an acceptable range for the specific catheter 100.

Handle 110 includes mouse control 111, an adjustable knob that provides two-dimensional control of cursor 230 of user interface 201, similar to mouse-control devices integral to some laptop computers. In a preferred embodiment, mouse control 111 can be torqued in various directions to achieve the two-dimensional control, and also pressed to provide a "click" or select function. Additionally or alternatively, an additional control of handle 110 can be used to perform the click function. The click function is used to select a graphic on visual display 220, such as icon 240, preferably an icon representation an ablation element 130 of carrier assembly 120. Numerous icons can be provided to the operator on display 220, such as icons that include information relating to system performance such as power being delivered, patient condition such as electrocardiogram (ECG) or tissue temperature, or a system parameter that can be set by an operator such as a target or threshold value. Alternatively, an icon or other graphic can be selected to modify the display mode, such as numeric form versus chart form, or a display mode characteristic such as font size or color.

Mouse control 111 can control cursor 230 via wireless transmissions using a wireless transceiver, not shown, or wired communication utilizing a wire integral to cable 202. Cursor 230 can be moved within visual display 220 of user interface 201 through manipulation of mouse control 111 and/or by other means, such as one or more controls integral to user interface 201 of RF delivery unit 200 or a computer mouse attached to RF delivery unit 200 (computer mouse not shown). In a preferred embodiment, visual display 220 is a touch screen display, permitting the selection of one or more icons, as well as other graphic images provided on display 220, by an operator pressing at the appropriate location on display 220. In another preferred embodiment, a visual representation of one or more of: the geometry of the electrodes 130, the geometry of one or more sensors, and the geometry of the patient's anatomy, is further provided. Information, such as system parameter information or other information, is displayed in relative geometric orientation to the one or more visual representations of catheter geometry and patient anatomy.

Also included in the system of the present invention is an additional device, handheld remote control 300. Remote control 300 includes a user interface with user input components such as buttons, and may include user output components such as an LCD screen or touch screen. Remote control 300 communicates with RF delivery unit 200 with wireless transmissions via an integral wireless transceiver than sends wireless information to RF delivery unit 200, and preferentially can also receive wireless communications from RF delivery unit 200 and other devices. In a preferred embodiment, remote control 300 is sterile and maintained in the sterile field of the patient, for use by one or more sterile operators, during the ablation procedure. In an alternative embodiment, remote control 300 is placed in a sealed, sterile bag and maintained in the sterile field. Remote control 300, in addition to mouse control 111 of ablation catheter 100 allow the clinician operator in the sterile field to modify one or more parameters of RF delivery unit 200, preferably not in the sterile field. Parameters may include parameters that cause one or more of: the activation or cessation of energy delivery; a change in the information displayed on visual display 220; a change in the manner in which information is displayed on visual display 220 such as a change in font size, graphic size, brightness or contrast; a change in alert status such as the muting of an alarm; or other function otherwise needed to be performed by an operator outside of the sterile field of the patient. In an alternative embodiment, remote control 300 has a wired connection to RF delivery unit 200.

Handle 110 also includes two push buttons, first button 116 and second button 117. These buttons can be used to perform one or more functions, and can work in cooperation with user input components of user interface 201 such that commands entered into user interface 201 set the action taken when either or both button 116 and button 117 are pressed. In a preferred embodiment, both button 116 and button 117 must be pressed simultaneously to deliver energy to one or more ablation elements of catheter 100. At the distal end of catheter shaft 101 is a circumferential band, band 104. Band 104 is preferably a visualization marker, such as a radiographic marker, ultrasound marker, electromagnetic marker, magnetic marker and combinations thereof. In an alternative embodiment, band 104 transmits or receives energy, such as when the marker is used as a ground or other electrode during an ablation. In another alternative embodiment, band 104 is an antenna used to determine the position of the distal end of catheter shaft 101 or the location of another component in relation to band 104. In another preferred embodiment, band 104 is used to store energy, such as capacitively stored energy that can be used to generate a magnetic field or to deliver ablation energy.

While the ablation catheter of FIGS. 3a and 3b is shown with an umbrella tip geometry, it should be appreciated that numerous configurations of carrier arms, such as spiral, zigzag, and other patterns could be employed. These carrier assemblies are configured to provide sufficient forces to maximally engage the appropriate ablation element with the tissue to be ablated, without adversely impacting neighboring structures and other tissues. While the carrier assembly 120 of FIG. 3a "folds in" during retraction of shaft 150, other collapsing configurations can be employed such as the "fold out" configuration of the catheter of FIG. 2a, or configuration in which the carrier assembly transforms from a spiral, zigzag, or other curvilinear shape to a relatively straight or linear configuration as it is retracted and captured by the lumen of catheter shaft 101. Electrodes 130 of carrier assembly of FIG. 3a are shown facing out from the distal end of shaft 101 such that advancement or "pushing" of carrier assembly 120 engages electrodes 130 with tissue. In an alternative embodiment, electrodes are positioned, alternatively or additionally, to face toward the distal end of shaft 101. These electrodes may be mounted to proximal arm segment 125 such that retraction or "pulling" of carrier assembly 120, once deployed, engages these rear-facing electrodes with tissue.

Ablation catheter 100 and RF delivery unit 200 are configured to ablate tissue with minimal power and precise control. RF Power levels are preferably less than 10 watts per electrode, and preferably 3 to 5 watts. Electrodes 130 are powered to reach an ablation temperature of approximately 60° C. The electrode geometries of the present invention, described in detail in reference to FIGS. 2a and 2b, provide numerous and varied benefits including enhanced cooling properties. Electrodes of the present invention are configured to rapidly transition from an ablation temperature of 60° C. to body temperature of 37° C., such as in a time period less than 10 seconds. These electrodes are further configured to rapidly increase from body temperature to ablation temperature, such as in a time period less than 5 seconds. In a preferred embodiment, bipolar RF energy is delivered subsequent to monopolar delivery. The electrodes and power delivery subsystems of the present invention are configured to allow the electrode and neighboring tissue to decrease in temperature during the bipolar RF energy delivery following the monopolar delivery. This bimodal, sequential power delivery reduces procedure time, allows precise control of lesion depth and width, and reduces large swings in ablation temperatures. In another preferred embodiment, the temperature in the tissue in proximity to the electrode actually continues to increase as the electrode temperature decreases, such as during the bipolar delivery following monopolar delivery. In an alternative embodiment, the monopolar delivery cycle, the bipolar delivery cycle, or both, are followed by a period of time in which no RF energy is delivered. During this "off" time period, no energy may be delivered or an alternative energy may be delivered such as cryogenic energy that actually decreases the temperature of the tissue in order to ablate.

In a preferred embodiment, parameters associated with the bipolar and monopolar energy delivery are adjusted during the procedure, automatically by the system and/or manually by the operator. The energy delivery parameters are adjusted by measured, calculated or otherwise determined values include those relating to: energy delivered measurements such as voltage or current delivered to an electrode; force or pressure measurement such as the force exerted by the carrier assembly as measured by an integral strain gauge; other ablation catheter or ablation system parameter; temperature of tissue; rate of change of temperature of tissue; temperature of an electrode or other ablation element; rate of change of temperature of an electrode or other ablation element; ECG; tissue thickness; tissue location; cardiac flow-rate; other patient physiologic and other patient parameters; and combinations thereof. The energy delivery drive parameters may be adjusted by a combination of these determined values. In order to automatically modify an energy delivery parameter, or to notify an operator of a condition, these determined values are compared to a threshold, such as via a threshold comparator integral to the interface unit of the present invention. Threshold values can be calculated by the system or can be entered by the operator into a user interface of the system.

Energy delivered measurements, such as current, voltage and power measurements, which may be compared to a threshold value, include average energy; instantaneous energy; peak energy; cumulative or integrated energy amounts; and combinations thereof. In the catheter and system of the present invention, average power is approximately 5 Watts and less, cumulative energy for a cycle of bipolar and monopolar delivery is typically less than 500 Watt-seconds and preferably less than 300 Watt-seconds (5 watts for 60 seconds). Each threshold value may change over time and may be adjustable by an operator such as via a password enabled user interface. Cumulative determined values, such as cumulative energy delivered and "time at temperature" values may be able to be reset, such as automatically by the system and/or manually by an operator. Automatic resets may occur at specific events such as each time an ablation element is repositioned on tissue or each time energy delivered changes states, including the switching of electrodes receiving energy or the completion of a monopolar-bipolar delivery cycle.

Determined values such as temperature measurements may be made from single or multiple sensors, such as multiple temperature sensors during a single ablation cycle. In a preferred embodiment, multiple sensors are used and the more extreme (e.g. a higher temperature) value is compared to a threshold. When the threshold comparator determines a particular threshold has been reached, the system can adjust or otherwise react in various ways. In a preferred embodiment, the system enters an alarm or alert state. In another preferred embodiment, the energy delivery transmitted to an ablation element is modified; such as to cease or reduce the amount of RF energy delivered to an electrode. Numerous energy delivery parameters can be modified including but not limited to: current level; voltage level; frequency (usually fixed at 500 KHz); bipolar delivery "on" times; monopolar delivery "on" times; no energy delivery "on" times; electrode selected such as bipolar return electrode selected; and combinations thereof.

The automatic and manual adjustments of the present invention are triggered by comparing a measured, calculated or otherwise determined value to a threshold. These adjustments improve numerous outcomes of the proposed ablation therapy including those associated with improved efficacy and reduced adverse events. Specific benefits include precision controlled depth and width of lesions through a combination of bipolar and monopolar sequential duty cycles. The system is adjustable by the operator to modify intended lesion geometry to safely avoid structures like pulmonary vein lumens and the esophagus, as well as work in portions of the atrial wall that require deep lesions to effectively interrupt aberrant pathways.

Figure 4:
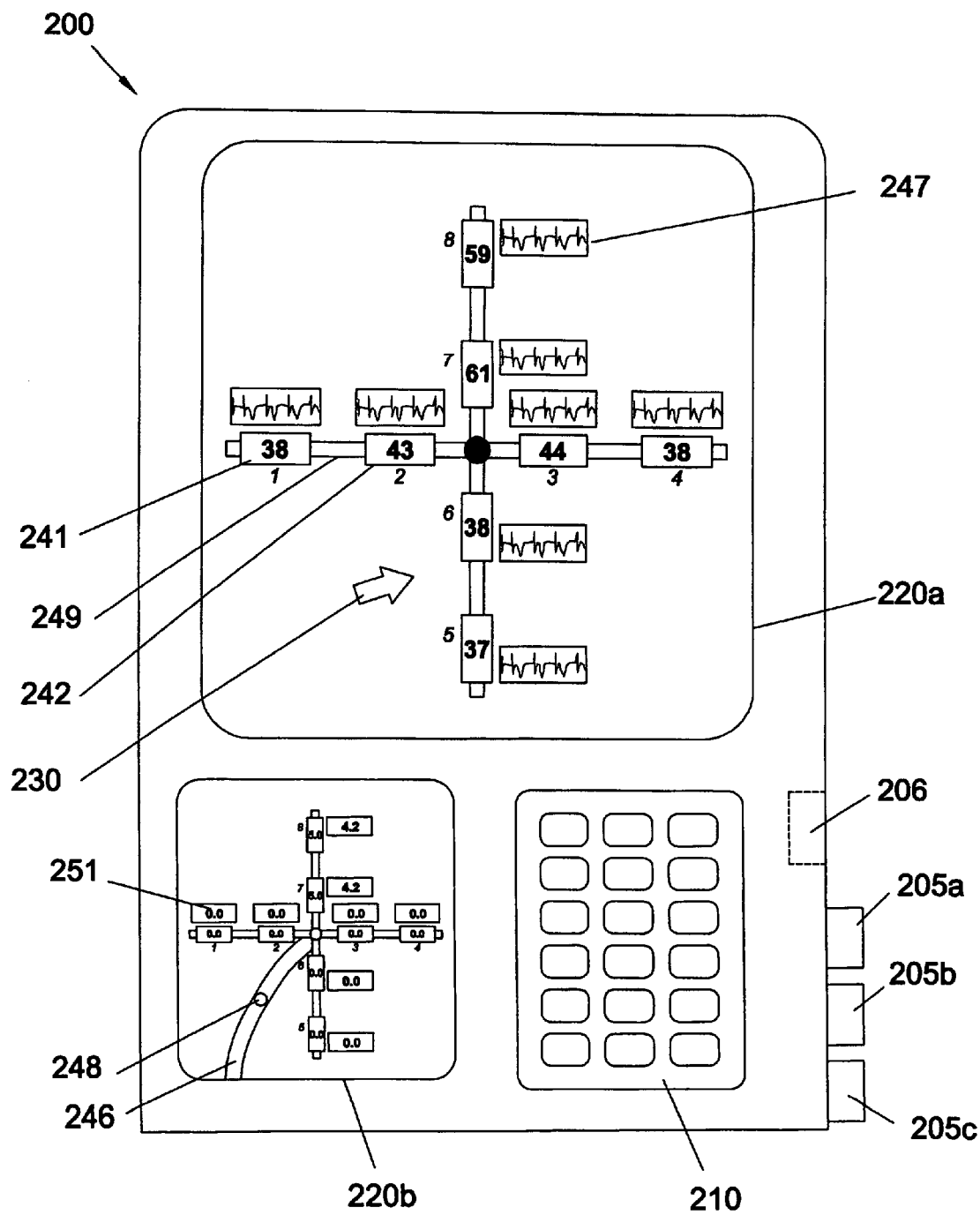
FIG. 4 illustrates a front view of an interface unit and user interface consistent with the present invention.

Referring now to FIG. 4, an interface unit of the present invention is illustrated. The interface unit is for attachment to an ablation catheter, not shown, that includes at least two ablation elements used to deliver energy to tissue. In a preferred embodiment, the at least two ablation elements of the ablation catheter are further configured to record electrical signals from tissue. The interface unit provides one or more forms of energy to the ablation catheter. The interface unit includes a visual display that provides a visual representation of the geometry of the at least two ablation elements. This visual representation allows numerous icons and other graphics, such as those containing system input or output information, to be visualized by one or more operators of the system in a geometric location relative to the geometric representation of the ablation elements. The functionality of the various icons and other graphics presented on the display may be modified or programmed by the user. That is, the icons may be programmed by the user to visually represent different system parameters and/or permit the modification of one or more system parameters. In an alternative or additional embodiment, the user can create a new icon, after which one or more functionalities can be assigned, by the user or otherwise, to the activation of that icon. Such enhanced visualization of information simplifies programming and use, especially with ablation catheters including larger number of ablation elements and/or complex ablation element patterns. Simplified use correlates to a shorter and safer procedure for the patient, and reduced costs for the healthcare system. Information, such as system parameter information, includes information related to values of parameters, on or off states of functions such as energy delivery and alarm functions, patient physiologic parameters such as tissue temperature and ECG, and other information used or produced by the system during the ablation and/or mapping procedure. Information may include numeric and/or or text values, and may be associated with a specific component of a catheter, such as a specific ablation or mapping element.

In a preferred embodiment, system parameter information displayed, selected and/or modified is selected from the group consisting of:
an energy delivery parameter such as the specific ablation element or elements selected for energy delivery, current, voltage, frequency, power, mode such as monopolar or bipolar mode, duration such as on time or off time, impedance, and type of energy to be delivered such as RF energy or ultrasound energy;
a sensor parameter such as selected sensor or selected multiple sensors, tissue contact measurement value; temperature, pressure, strain and ECG, cardiac flow rate, tissue thickness and tissue location;
an alarm parameter such as an alarm on state;
an additional catheter parameter such as distance between two ablation elements, distance between a sensor and an ablation element, and distance between two sensors;
an additional system component parameter;
a target value for a system parameter;
a threshold value for a system parameter;
a current ("real time") value for a system parameter;
as well as derivatives (such as mathematically processed values) and combinations thereof.

Referring back to FIG. 4, the interface unit of the present invention is comprised of RF delivery unit 200, which is configured to provide RF energy to an ablation catheter. RF delivery unit 200 is comprised of a single discrete component including attachment ports, user input components and user output components. In an alternative embodiment, RF delivery unit 200 includes multiple discrete components such as a RF generator unit and one or more separate video monitors. RF delivery unit 200 includes multiple attachment ports, port 205*a*, 205*b* and 205*c*. Port 205*a* is for attachment to an ablation catheter, and includes energy delivery conduit attachment such as a wire for delivering the RF energy, wires and other conduits such as fiber optic cables for transmitting or receiving light signals and energy. Port 205*b* and port 205*c* may be attached to the same ablation catheter, a second ablation catheter, and/or another catheter or other device. Each attachment port may be configured to send or receive power or information signals, in various forms including electrical, light and fluid such as cryogenic fluid. Attachment ports may provide connections for pressurized air or saline for balloon inflation, flow of fluid for ablation and/or cooling, or other connection needs.

Unit 200 includes two visual displays, each preferably a touch screen display, first visual display 220*a* and second visual display 220*b*. Each display is configured to provide information to one or more operators of the system as well as allow these operators to modify a system parameter or modify which information is to be displayed and the form in which it is displayed. The display may be preconfigured by the manufacturer so that the operator or operators are prived with customized information for future selection and/or activation by the operator's choice. The programming may be performed with an input device such as the touch screen display, the keypad 210, cursor 230, mechanical switches, or the like. In some cases the functionality of the input devices themselves may also be programmed by the operator. One or more selection means can be used to select an icon or other graphic displayed unit 200. Keypad 210 is a membrane keypad mounted to the front panel allowing an operator to press one or more keys to select and modify displayed information. Wireless transceiver 206 is a wireless communication element of the present invention and allows a separate component, such as an ablation catheter of the present invention, also including wireless communication means, to send data in order to select and modify displayed information. Alternatively, an ablation catheter can transmit wired communication signals such as through attachment port 205*a*.

As shown in FIG. 4, first visual display 220*a*, preferably a touch screen display, provides a visual representation of a four-arm umbrella shaped carrier assembly, such as of the carrier assembly of the ablation catheter of FIG. 2*a*. The visual representation of the carrier assembly includes eight electrode icons, labeled "1" thru "8" on visual display 220*a*. The electrode icons, such as first electrode icon 241 for electrode 1 and second electrode icon 242 for electrode 2, are shown mounted to a visual representation of the carrier arms, such as icon 241 and icon 242 mounted to carrier arm 249. Shown on each ablation element icon is temperature information for that electrode, for example degrees Celsius information "38" for electrode 1 and "43" for electrode 2 (two electrodes not receiving ablation energy), and "61" for electrode 7 and "59" for electrode 8 (two electrodes receiving ablation energy). Adjacent to and geographically associated with each ablation icon is an ECG information icon, such as ECG information icon 247. The visual representation can be displayed "actual size" in a 1 to 1 relationship, in an enlarged view, or in a miniaturized or reduced view.

In embodiments in which first visual display 220*a* is a touch screen, an icon can be selected by pressing the part of the display in which the icon appears. Additionally or alternatively, the icon can be selected by moving cursor 230 to a location at or above the icon, such as with a mouse (not shown) attached to unit 200, a control such as a control on keypad 210 of unit 200, or a remote cursor control device such as a handle control described in reference to FIG. 3*a* and FIG. 5. When cursor 230 is placed above a particular icon, a click function such as a mouse click or keyboard click function can be used to select the icon. Once selected, an icon can be changed in the value of information displayed or the form in which the information is displayed utilizing one or more of the controls used to position the cursor.

Unit 200 of FIG. 4 further provides a second display, visual display 220*b* that includes a second visual representation of the geometry of the ablation elements of a catheter that is attached to unit 200, catheter not shown. Display 220*b* includes an array of electrode icons, similar to the visual representation provided on display 220*a*. Adjacent to or above the electrode icons is information that is related to each specific electrode, such as target power level information provided on icon 251 neighboring electrode 1, and the actual power level information provided on or within the icon for electrode 1. This particular presentation of current and target information, a preferred embodiment of the present invention, provided in the actual geometric configuration of the ablation catheter, such as the four arm ablation catheter shown, provides a greatly simplified user interface for the clinician or other operator to rapidly and simply interpret. Further provided on visual display 220*b* is a visual representation of the distal end of the ablation catheter, catheter icon 246, including a visual representation of an electrode mounted on the catheter body, catheter electrode icon 248. Catheter electrode icon 248 represents an electrode mounted on the distal end of the tubular body member of a catheter. Alternatively, icon 248 may represent a sensor, such as a temperature sensor. Information associated with the geometric location of icon 248 is displayed on or near icon 248, information not shown.

The visual displays of unit 200 of FIG. 4 display system parameter information in geometric relation to a visual representation of one or more parts of an attached ablation catheter. The system parameter information displayed may be based on signals received from one or more sensors integral to the attached ablation catheter. The system parameter information may include patient physiologic information such as ECG information received from a mapping electrode or a combined ablation and mapping electrode. In a preferred embodiment, ECG information is provided simultaneous with energy delivery, such as when delivery unit 200 includes an "active" filter which is configured to actively remove noise signals generated by the concurrent tissue ablation and "picked up" by the electrode provide the mapping electrode, for example, the same electrode also delivering the ablation energy. The active filter is configured to take advantage of the known frequency, voltage and current being supplied to the electrode by unit 200, to actively separate the resultant noise from the true ECG signal.

The information displayed on visual display 220*a* or 220*b* can be provided in one or more modes selected from the group consisting of: alphanumeric text; a graph such as a line or bar graph; a chart such as a pie chart; and combinations thereof. In a preferred embodiment, the information mode of a set of information is configured to be adjusted by a user, such as by selecting information with a control on the ablation catheter or unit 200. In another preferred embodiment, the mode of a set of information adjusts automatically, such as when the information changes in value.

The information displayed on visual display 220*a* or 220*b* can be provided with one or more mode characteristics selected from the group consisting of: size such as font size; font type such as Arial or Helvetica; graphic size, color; contrast; hue; brightness; and combinations thereof. In a preferred embodiment, the information mode characteristic of a set of information is configured to be adjusted by a user, such as by selecting information with a control on the ablation catheter or unit 200. In another preferred embodiment, the mode characteristic of a set of information adjusts automatically, such as when the information changes in value. Numerous configurations of information colors, sizes and boldness can be used to simplify use, and avoid potentially dangerous situations such as an increase in font size or boldness when a system parameter approaches an unsafe state, such as an unsafe temperature set by a threshold. In a preferred embodiment, the information displayed is actual or current tissue temperature information and the information displayed is shown in blue font when the temperature approximates body temperature, and transitions to shades of red as the temperature rises. In another preferred embodiment, temperature values are displayed in blue when the temperature is at or below a target temperature. Temperature is displayed in yellow when temperatures are above the blue temperature range but still within an allowable specification (e.g. a second target level). Temperature is displayed in red when above the yellow temperature range (e.g. at an undesired or unacceptable level). In yet another preferred embodiment, the displayed information transitions from a lighter shade to a darker shade as the value of a piece of information increases. In yet another preferred embodiment, the information displayed is target information, such as target temperature information, and the information is displayed in blue or yellow, blue representing a temperature level below the temperature level represented by yellow. In yet another preferred embodiment, unit 200 further comprises an audio transducer, not shown. The audio transducer emits an alert sound to the operator to signify one or more of: an icon or other displayed information is selected; information is modified; a threshold is reached by a system parameter; and combinations thereof.

The information displayed on visual display 220a or 220b can be of one or more information types selected from the group consisting of: current, historic, target, threshold, and combinations thereof. Current information may be real time (current time) information selected from the group consisting of: ECG or recognized ECG pattern; energy delivery value such as power, voltage or current; temperature; rate of temperature change; distance; force; pressure; location; and combinations thereof. Target information may be information selected from the group consisting of: recognized ECG pattern; energy delivery value such as power, voltage or current; temperature; rate of temperature change; distance; force; pressure; location; and combinations thereof. Threshold information may be information selected from the group consisting of: recognized ECG pattern; energy delivery value such as power, voltage or current; temperature; rate of temperature change; distance; force; pressure; location; and combinations thereof. In a preferred embodiment, related current and target information are displayed simultaneously. In another preferred embodiment, related current and threshold information are displayed simultaneously. In yet another preferred embodiment, multiple pieces of information of the same information type are displayed with the same display mode characteristic. In yet another preferred embodiment, multiple pieces of information of the same information type are displayed in the same color.

System parameter and other information measured, calculated and otherwise determined by the system of the present invention may include similar information from two or more system components, such as temperature information received from two or more sensors. An operator of the system may prefer to only view the extreme conditions, such as the "worst-case" conditions, such as the highest of all temperatures received. In a preferred embodiment, worst-case information is displayed on visual display 220a or 220b in a different mode or with a different mode characteristic than non worst-case information. In another preferred embodiment, worst-case information is shown in redundant form on either or both displays 220a and 220b, such as in one location in proximity to the element producing the associated information, and in a separate "worst-case location", providing a standard location for the operator to view to see the worst-case information.

In a preferred embodiment, the attached ablation catheter includes one or more sensors, and a visual representation of the sensor geometry is shown on display 220a, 220b or both. Sensor geometry may include thermocouples integral to one or more electrodes, or a separate temperature sensor shown in relation (relative distance) to one or more neighboring electrodes. In another preferred embodiment, the ablation catheter includes an elongate body member, and a visual representation of the elongate body member is provided on display 220a, 200b or both. One or more system parameters are shown in geometric relation to the distal portion of the elongate body member.

In another preferred embodiment, a visual representation of the patient's anatomy, such as the anatomy neighboring the carrier assembly of the attached ablation catheter, is shown of display 220a, 220b, or both. The displayed patient's anatomy preferably is a visual representation of the patient's heart, such as an atrium of the heart. Unit 200 may include a library of typical anatomical landscapes, and unit 200 is configured to allow an operator to select an appropriate anatomical image, and position the image relative to the visual representation of the ablation elements or a different visual representation described hereabove. Alternatively or additionally, the image may be generated or partially generated from information received from an imaging device, all not shown, such as a: fluoroscope, external ultrasound device, internal ultrasound device, MRI unit, infrared camera, and combinations thereof. The imaging device may be included in the ablation catheter or inserted within a lumen of the ablation catheter, such as an ultrasound catheter or a fiber optic camera device. The fiber optic camera may comprise an inserted fiber optic cable with a wide-angle lens on the fiber optic's distal end, and a fiber optic receiving camera on the fiber optic's proximal end.

In a preferred embodiment, bipolar RF ablation energy is combined with monopolar RF energy to form specifically sized and positioned lesions. Energy can be delivered to multiple electrodes or multiple pairs of electrodes simultaneously or sequentially. Selecting which electrodes are to receive energy, and in which form (monopolar or bipolar), is greatly simplified with the user interfaces of the present invention. In a preferred embodiment, two electrodes are selected for receipt of bipolar energy by one or more of: dragging a finger or stylus device from a first electrode icon, such as electrode icon 241, to a second electrode icon such as electrode icon 242; selecting a first electrode icon, moving a cursor from the first electrode icon to a second electrode icon, and selecting the second electrode icon; and combinations thereof.

The interface unit 200 may be programmable so that energy is delivered to certain electrodes or pairs of electrodes in a predetermined sequence or sequences determined and/or selected by the operator. The predetermined sequence may depend on the value of other system or ablation parameters that have previously been selected. For instance, if the operator selects a particular carrier arm, one of the predetermined sequences may automatically select to receive energy the innermost electrode on that arm or any of the other electrodes on that arm. Additionally, in bipolar mode, if the operator selects a particular electrode on a particular carrier arm to receive energy, a predetermined sequence may be programmed to automatically select another electrode(s) on that arm (or a different arm) which has a preselected position relative to the particular electrode selected by the operator. For instance, the second electrode that is automatically selected to receive energy may be the next electrode inward (or outward) from the first electrode selected by the operator. Alternatively, the second electrode that is automatically selected may be the corresponding electrode on an adjacent arm (determined in a clockwise or counterclockwise direction along the carrier array). As another example, if the operator selects a particular arm for unipolar operation only, a predetermined (e.g., outermost) electrode on that arm is automatically selected. A button on the keypad may allow the user to toggle between the various electrodes in the event that a different electrode is desired. Another button (or other input means) may be employed to override the programming so that the selection of electrodes does not necessarily follow one of the predetermined sequences.

Figure 6:
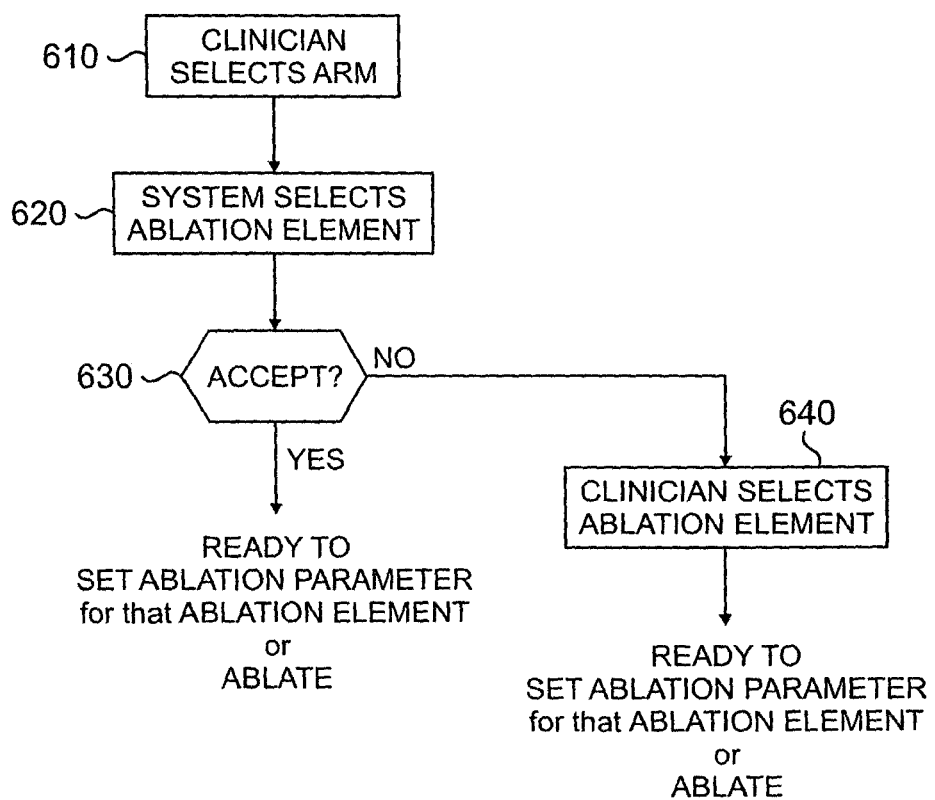
FIG. 6 is flowchart summarizing a programmed sequence used to select ablation elements or electrodes.

FIG. 6 is flowchart summarizing a programmed sequence used to select ablation elements or electrodes. In step 610 the clinician or other operator selects a carrier arm to which energy is to be delivered. In step 620, the system automatically selects a particular electrode or electrode on the selected arm. The operator is then given the option of accepting or rejecting the automatic selection in step 630. If the operator accepts the automatic selection, the various ablation parameters are set for that electrode (if needed) after which the ablation process may begin. If the operator does not accept the automatic selection, then in step 640 the operator overrides the automatic selects and makes his or her own selection, after which the various ablation parameters are once again set for the operator-selected electrode (if needed).

Referring back to FIG. 4, graphic display unit 200 may include means of controlling a robotic ablation and/or mapping catheter, not shown, such as a catheter whose tip orientation, carrier assembly deployment condition or other catheter geometry orientation is remotely controllable. The robotic catheter typically comprises one or more linear or rotary actuators, such as motors or solenoids, which are operably attached to elongate, flexible linkage members slidingly received by the catheter's shaft, all not shown. The actuators are activatable by an operator via a control on graphic display unit 200, such as an icon on visual display 220a or a button on keypad 210. The linkage members, attached at their proximal end to an actuator such as via a cam or other mechanical advantage assembly, are attached at their distal end to an ablation and/or mapping carrier assembly, to a distal portion of the catheter shaft, or to another catheter geometry modifying component. Advancement and/or retraction of a linkage cause the catheter's geometry to controllably, repeatably and reversibly change. In this alternative embodiment, first visual display 200a and/or second visual display 220b display the current geometric configuration of one or all of the portions of the robotically controlled catheter that can be remotely changed in its orientation (e.g. via known actuator condition and/or information from a catheter sensor). One or more controls of graphic display unit 200, such as a button on keypad 210, or a control icon on visual display 220a or 220b can be used to manipulate or otherwise modify one or more catheter orientations, such as by sending signals to an actuator operably connected to a linkage. As the linkage is advanced or retracted via a control on graphic display unit 200, the current displayed geometry of the catheter changes, such as by changing in real time, to provide visual feedback to the operator regarding catheter orientation. In a preferred embodiment, graphic display unit 200 receives information from one or more sensors integral to the robotically controlled catheter, such that closed loop catheter geometry information is provided to graphic display unit 200. Sensors may include strain gauges, magnetic sensors and other sensors. The visual feedback information provided on graphic display unit 200 can be used by an operator is use of the catheter, in addition to visual information received via a x-ray image provided through use of fluoroscopy and one or more radiographic portions of the catheter. Fluoroscopic images are often plagued with inaccuracies due to parallax and other non-orthogonal imaging perplexities. These issues can be avoided by the catheter specific geometry information provided to the operator by graphic display unit 200. In an alternative or additional embodiment, an integral shape memory component, such as a shape memory polymer or an embedded shape memory alloy wire, provides geometry information to graphic display unit 200. In a similar fashion to the remote control described above, an operator used a control on graphic display unit 200 to modify the geometry of a portion of the catheter by changing the shaped memory component condition. Simultaneous with the geometry change, a visual representation of the current geometry is displayed on display 200a and/or 200b.

Figure 5:
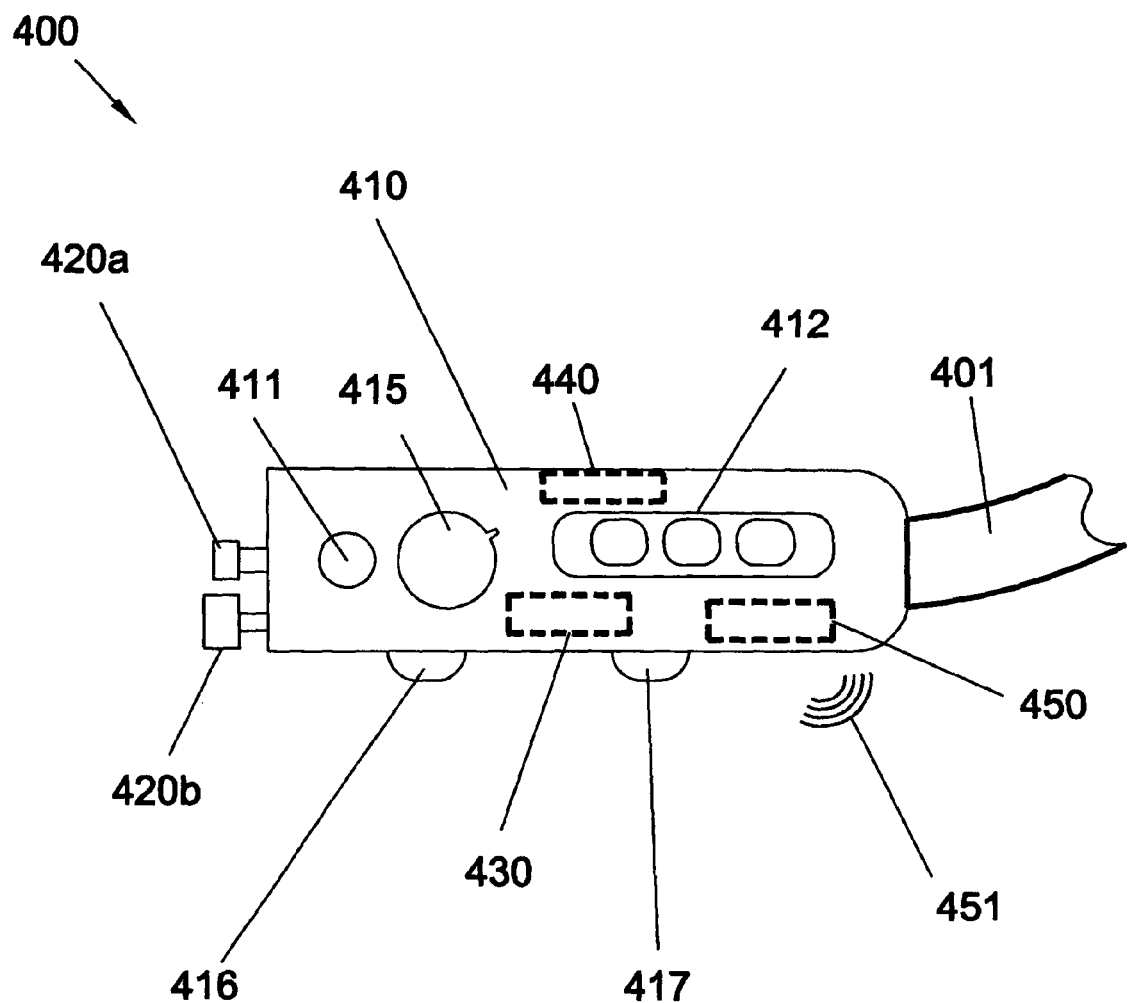
FIG. 5 illustrates a top view of a handle of a catheter device consistent with the present invention.

Referring now to FIG. 5, a catheter of the present invention is illustrated. The catheter is for performing a sterile medical procedure and for insertion into a body cavity of a patient. An integral control assembly is included for controlling a separate medical device. Catheter 400 includes handle 410 mounted on its proximal end. Handle 410 is mounted to a flexible shaft, such as a shaft configured for percutaneous insertion and advancement in the vasculature of a patient, to perform a medical procedure such as an interventional therapeutic or diagnostic procedure. On the proximal end of handle 410 are two attachment ports, first attachment port 420a, such as an attachment port for an ECG mapping system and attachment port 420b, such as an attachment port for an ablation energy delivery unit. Further included on handle 410 are two buttons, first button 416, such as a button to initiate energy delivery, and button 417 such as a button to reset an alarm condition.

Handle 410 further includes knob 415, which is operably attached to a pull-wire that extends near the distal end of shaft 401, pull-wire and distal end not shown. Rotation of knob 415 causes the distal end of shaft 401 to deflect, such as to orient an advancable tube toward a target. Battery 430 is integral to handle 410, and provides power to one or more electronic components or assemblies of handle 410. One electronic component of handle 410 is tactile transducer 440, preferably a miniature motor assembly with an eccentric weight on its shaft. Rapid rotation of the shaft causes an angular momentum change such that an operator holding handle 410 can be notified of a condition such as an alarm condition.

Handle 410 further includes wireless transceiver 450, a wireless communication assembly that transfers information via RF communication 451 or other wireless communication means to a properly configured wireless receiver or transceiver. Handle 410 includes various input components, mouse 411 and keypad 412. Keypad 412 is preferably a waterproof, membrane keypad with multiple activatable switches. Mouse 111 is preferably a waterproof, adjustable knob that provides two-dimensional control of a display cursor, similar to mouse-control devices integral to some laptop computers. Handle 410 further includes one or more electronic components, not shown, to process signals received from mouse 411 and keypad 412 and produce signals to be transmitted by wireless transceiver 450. The wireless information is transmitted, such as in a secure wireless transmission, to a separate medical device, in order to control or otherwise change the state of the separate medical device.

The separate medical device, not shown but preferably a device maintained out of the sterile field of the ablation catheter 400, includes one or more control functions applicable to keypad or mouse control. In a preferred embodiment, the separate medical device to be controlled is selected from the group consisting of: a fluoroscope system; an ultrasound system; a data management system such as a patient information system; a cardiac defibrillation system; a cardiac monitoring system; an esophageal probe system; and combinations thereof. In a preferred embodiment, wireless transceiver 450 sends wireless communications 451 to multiple separate medical devices. Embedded in the transmissions is preferably an ID, which signifies and/or identifies the particular device that is intended to respond to the transmitted command. In an alternative embodiment, wireless transceiver 450 receives information and/or commands from a separate medical device. Received information may indicate a remote device is in an alarm state, and tactile transducer 440 may alert the operator of the remote device's alarm state.

It should be understood that numerous other configurations of the systems, devices and methods described herein may be employed without departing from the spirit or scope of this application. The ablation catheter includes one or more ablation elements such as electrodes. These electrodes may include various cross-sectional geometries, projecting fins, energy delivering portions and non-energy delivering portions, and other varied features. The systems of the present invention are configured to automatically, semi-automatically or manually adjust various ablation, mapping and other system parameters such as the energy applied to the ablation elements such as by adjusting one or more of the following: the level or amount of energy delivered; type of energy delivered; drive signal supplied such as monopolar and bipolar; phasing, timing or other time derived parameter of the applied energy; and combinations thereof.

In some cases the ablation parameters may be adjusted to their appropriate values with the use of macros to automate frequently-used combinations of setting, parameters and/or sequences. For instance, some macros may be employed in which two or more ablation parameters are set by a single user action. The macros may be pre-loaded into the interface unit or they may be programmed by the user via a programming interface incorporated in the interface unit. For example, when the user selects a particular ablation element or ablation element pair, one macro may establish values for the form of energy to be delivered to it, its power, duration and maximum temperature. Other ablation parameters that may be incorporated into macros include, without limitation, energy parameters (e.g., the form or type of energy, duty cycle parameter, power, monopolar and/or bipolar energy), ablation catheter parameter (e.g. catheter model number or configuration), patient parameter (e.g., a patient physiologic parameter such as heart wall thickness or an electrocardiogram parameter) anatomical location parameter (e.g. a location for an ablation to be performed such as the septum between the left and right atria) and a temperature parameter (e.g. a target ablation temperature or a maximum ablation temperature). In a preferred embodiment, a uniformity of temperature parameter is assigned to and/or activatable by a macro. This uniformity of temperature may be a comparison of temperature between two or more temperature sensors such as thermocouples. The thermocouples may be integrated into the ablation catheter such that a first sensor is indicative of tissue temperature and a second sensor is indicative of neighboring blood. Each thermocouple may be proximate a single ablation element, or an ablation element pair such as a pair used to deliver bipolar radiofrequency energy.

Some of the macros may be learning macros in which previously used combinations of settings, parameters and/or sequences are automated over time. Such learning macros may be defined for certain procedures, patient parameters, ablation elements, and the like.

The macros may be established and implemented using any of the aforementioned input devices associated with the interface unit 200 such as the touch screen display 220*a*, keypad 210 and/or cursor 230. For instance, a particular macro may be initiated by use of a predefined button on the keypad 210. The association between the macros and the buttons on the keypad may be programmed by the user. Of course, other devices such as switches and the like may be used to establish and/or implement the macros. For instance, upon establishing a new macro, icons on the touch screen display 22*a* may be sequentially selected to record various ablation parameters associated with the element represented by the icon. If a touch screen display is not employed, the icons or other macro activation elements may be selected by use of cursor 230 and a cursor controlling device such as a mouse or kepad. In a preferred embodiment, multiple components can be used to select, activate or adjust an icon or other activatable adjustment means. In another preferred embodiment, a selection component is located in the sterile field of the patient (e.g. a cursor control element in the handle of an ablation and/or mapping catheter of the present invention).

In some systems, the interface unit may include an autocomplete function in which the first few characters of an alphanumeric character string are entered by a user and automatically compared by the system to previously entered character strings in order to reduce the number of steps required to complete the entry. The characters that are entered may also be compared to an electronic database or library of appropriate terms to complete the entry. The database or library may include, without limitation, historic system parameter data as well as terms pertaining to patient specific data, operator specific data, manufacturer-supplied data and the like. The historic system parameter data may include both data entered by an operator in previous use of the system, as well as data recorded by the system during its use such as recorded temperature or power information achieved during use. Historic information may include information relevant to a first interface unit that has been uploaded into a second interface unit, such as information transferred through electronic transfer media (e.g. USB storage device) and/or electronically networked components.

The autocomplete function may be based on a word prediction algorithm that locates the identical or best match when comparing the entered characters to previously entered character strings that have been previously entered or otherwise are stored in a database of relevant information. In a preferred embodiment, the library is segregated into sub-libraries by system parameter type (e.g. temperature information is segregated from power information such that autocomplete is more appropriate). The algorithm that is employed may successively compare the partially entered character string with a library or sub-library set of values, each time a new character is entered by the user, until an appropriate match is determined. When a match is found, the user may be given an opportunity to accept or reject the selection, such as via a confirm function decribed herebelow. If no match is found, the user simply completes the entry in the normal manner. If a match is found, but the user continues to enter additional characters, the autocomplete function is disabled. If more than one match is found, one or more of them may be displayed (possibly in a rank order beginning with the best or most likeliest match) and optionally selected by the user.

In a preferred embodiment, the system of the present invention includes a confirm function which must be activated in order for a macro, such as an autocomplete macro, to be accepted or initiated. The confirm function may be activated through the selection of an icon (e.g. a touch screen icon) or a switch (such as a membrane switch integral to the handle of an ablation catheter). In a preferred embodiment, the confirm function icon is displayed prior to macro initiation, and the operator selects the icon to initiate the macro.

The wireless transmissions of the present invention preferably include information that assures secure communications between the two devices. Handshaking, error identification and correction methods, and other wireless communication protocols are preferably employed to assure safe and effective therapeutic results. In a preferred embodiment, wireless communications include a unique ID for either or both devices in communication. Wireless communication means may include one-way or two-way capabilities. The selection means of the present invention can take on various forms selected from the group consisting of: control on the interface unit, device in communication with interface unit such as wired or wireless mouse or tablet; control on ablation catheter such as a wired or wireless control on handle of ablation catheter; control on separate therapeutic device; a verbal command such as a recognized voice command made by an operator of the system; and combinations thereof.

The operators of the present invention may take on various forms, such as electrophysiologists that perform cardiac arrhythmia treatment procedures in a catheterization or electrophysiology lab. Multiple operators may be involved, such as the clinician performing the procedure and residing in the sterile field of the patient, and an assistant outside the sterile field and involved with changing one or more system parameters.

The ablation elements of the present invention are attached to energy delivery conduits that carry the energy to the electrode that is supplied by the interface unit. RF electrodes are connected to wires, preferably in a configuration with individual wires to at least two electrodes to allow independent drive of the electrodes including sequential and simultaneous delivery of energy from multiple electrodes. Alternative or additional energy delivery conduits may be employed, such as fiber optic cables for carrying light energy such as laser energy; tubes that carry cryogenic fluid for cryogenic ablation or saline for saline mediated electrical energy ablation; conduits for carrying sound energy; other energy delivery conduits; and combinations thereof.

The ablation elements of the catheter of the present invention can additionally or alternatively perform the function of cardiac mapping, such as metal plate or band electrodes integral to the carrier assembly which record electrical activity present in tissue. In these embodiments, the interface unit is electrically connected to these mapping elements, receives the electrical signals recorded from the tissue in contact with the mapping elements, and processes these signals to display ECG and other relevant signal information. The interface unit may or may not also provide ablation energy to the catheter (e.g. if ablation elements are also integral to the catheter). The various ablation system user interface features and methods of the present invention, described hereabove in reference to one or more ablation elements, are directly applicable to embodiments involving mapping elements and a mapping element user interface. A mapping system visual display may provide a visual representation of the geometry of one or more mapping elements. The mapping system visual display may include an operator selectable icon, such as an icon representing a mapping element. The mapping system user interface may include a programming interface with a macro function that initiates two commands with a single action. The mapping system user interface may include an autocomplete function to automatically complete an alphanumeric string that has been partially entered by an operator. The mapping system user interface may include an operator programmable adjustment means. The mapping system user interface may include a programming interface which provides means of selecting at least one arm of a carrier assembly of a mapping catheter. After the specific arm is chosen by an operator, a specific mapping element is automatically selected to have its information displayed on a visual display of the system. The mapping system user interface may provide a visual representation of the geometry of one or more mapping elements as well as a visual representation of a robotically maneuverable segment.

The system includes multiple functional components, such as the ablation catheter, and the interface unit. The interface unit preferably comprises: energy supply means and a user interface; calculating means for interpreting data such as mapping data and data received from one or more sensors; and means of comparing measured, calculated or otherwise determined values to one or more thresholds, such as a temperature or energy delivery threshold. The interface unit further includes means of adjusting one or more system parameters, such as the amount type, or configuration of energy being delivered, when a particular threshold is met. The ablation catheter includes ablation elements for delivering energy to tissue such as cardiac tissue. Cardiac tissue applicable for ablation includes left and right atrial walls, as well as other tissues including the septum and ventricular tissue. The ablation catheter of the present invention includes a flexible shaft with a proximal end, a distal end, and a deployable carrier assembly with multiple ablation elements. The flexible shafts may include one or more lumens, such as thru lumens or blind lumens. A thru lumen may be configured to allow over-the-wire delivery of the catheter or probe. Alternatively the catheter may include a rapid exchange sidecar at or near its distal end, consisting of a small projection with a guidewire lumen therethrough. A lumen may be used to slidingly receive a control shaft with a carrier assembly on its distal end, the carrier assembly deployable to exit either the distal end or a side hole of the flexible shaft. The advancement of the carrier assembly, such as through a side hole, via controls on the proximal end of the device, allows specific displacement of any functional elements, such as electrodes, mounted on the carrier assembly. Other shafts may be incorporated which act as a rotational linkage as well as shafts that retract, advance or rotate one or more components. A lumen may be used as an inflation lumen, which permits a balloon mounted on a portion of the exterior wall of the flexible shaft to be controllably inflated and deflated. The balloon may be concentric or eccentric with the central axis of the shaft, it may be a perfusion balloon, and may include an in-line pressure sensor to avoid over-pressurizing. A lumen may be used to receive a rotating linkage, such as a linkage used to provide high-speed rotation of an array of ultrasound transducers mounted near the distal end of the linkage. Each device included in a lumen of the flexible shafts may be removable or configured to prevent removal.

The ablation catheter of the present invention may include one or more functional elements, such as one or more location elements, sensors, transducers, antennas, or other functional components. Functional elements can be used to deliver energy such as electrodes delivering energy for tissue ablation, cardiac pacing or cardiac defibrillation. Functional elements can be used to sense a parameter such as tissue temperature; cardiac signals or other physiologic parameters; contact with a surface such as the esophageal or atrial walls of a patient; an energy parameter transmitted from another functional element such as amplitude, frequency; phase; direction; or wavelength parameters; and other parameters. In a preferred embodiment of the present invention, the ablation catheter includes multiple functional elements. In another preferred embodiment, the ablation catheter includes a deflectable distal end; such as a deflected end that causes one or more functional elements to make contact with tissue. Deflection means may include one or more of: a pull wire; an expandable cage such as an eccentric cage; an expandable balloon such as an eccentric balloon; an expandable cuff; a deflecting arm such as an arm which exits the flexible catheter shaft in a lateral direction; and a suction port.

The ablation catheter of the present invention preferably includes a handle on its proximal end. The handle may be attached to an outer sheath, allowing one or more inner shafts or tubes to be controlled with controls integral to the handle such as sliding and rotating knobs that are operable attached to those shafts or tubes. Alternatively, the handle may be attached to a shaft that is slidingly received by an outer sheath, such that an operator can advance and retract the shaft by advancing and retracting the handle and holding the sheath in a relatively fixed position. The handle may include one or more attachment ports, such as attachment ports which electrically connect to one or more wires; ports which provide connection to optical fibers providing laser or other light energies; ports which fluidly connect to one or more conduits such as an endoflator for expanding a balloon with saline or a source of cooling fluids; and combinations thereof. Other controls may be integrated into the handle such as deflecting tip controls, buttons that complete a circuit or otherwise initiate an event such as the start of energy delivery to an ablation element. In addition, the handle may include other functional components including but not limited to: transducers such as a sound transducer which is activated to alert an operator of a change is status; a visual alert component such as an LED, a power supply such as a battery; a lock which prevents inadvertent activation of an event such as energy delivery; input and output devices that send and receive signals from the interface unit of the present invention; and combinations thereof.

The interface unit of the present invention provides energy to the ablation elements of the ablation catheter. In preferred embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy and physical energy such as pressurized fluid; radiation; and combinations thereof. The ablation elements can deliver energy individually, in combination with or in serial fashion with other ablation elements. The ablation elements can be electrically connected in parallel, in series, individually, or combinations thereof. The ablation catheter may include cooling means to prevent undesired tissue damage and/or blood clotting. The ablation elements may be constructed of various materials, such as plates of metal and coils of wire for RF or other electromagnetic energy delivery. The electrodes can take on various shapes including shapes used to focus energy such as a horn shape to focus sound energy, and shapes to assist in cooling such as a geometry providing large surface area. Electrodes can vary within a single carrier assembly, such as a spiral array of electrodes or an umbrella tip configuration wherein electrodes farthest from the central axis of the catheter have the largest major axis. Wires and other flexible energy delivery conduits are attached to the ablation elements, such as electrical energy carrying wires for RF electrodes or ultrasound crystals, fiber optic cables for transmission of light energy, and tubes for cryogenic fluid delivery.

The ablation elements requiring electrical energy to ablate require wired connections to an electrical energy power source such as an RF power source. In configurations with large numbers of electrodes, individual pairs of wires for each electrode may be bulky and compromise the cross-sectional profile of the ablation catheter. In an alternative embodiment, one or more electrodes are connected in serial fashion such that a reduced number of wires, such as two wires, can be attached to two or more electrodes and switching or multiplexing circuitry are included to individually connect one or more electrodes to the ablative energy source. Switching means may be a thermal switch, such that as a first electrodes heats up, a single pole double throw switch change state disconnecting power from that electrode and attaching power to the next electrode in the serial connection. This integral temperature switch may have a first temperature to disconnect the electrode, and a second temperature to reconnect the electrode wherein the second temperature is lower than the first temperature, such as a second temperature below body temperature. In an alternative embodiment, each electrode is constructed of materials in their conductive path such that as when the temperature increased and reached a predetermined threshold, the resistance abruptly decreased to near zero, such that power dissipation, or heat, generated by the electrode was also near zero, and more power could be delivered to the next electrode incorporating the above switching means.

The interface unit of the present invention includes a user interface including components including but not limited to: an ultrasound monitor such as an ultrasound monitor in communication with one or more ultrasound crystals near a temperature sensor of an esophageal probe or ultrasound crystals within an electrode carrier assembly of the ablation catheter; an x-ray monitor such as a fluoroscope monitor used to measure the distance between two or more location elements; other user output components such as lights and audio transducers; input components such as touch screens, buttons and knobs; and combinations thereof. In a preferred embodiment, the interface unit provides functions in addition to providing the energy to the ablation catheter including but not limited to: providing a cardiac mapping function; providing cardiac defibrillation energy and control; providing cardiac pacing energy and control; providing a system diagnostic such as a diagnostic confirming proper device connection; providing the calculating function of the present invention; providing a signal processing function such as interpreting signals received from one or more sensors of a probe, such as an esophageal probe, and/or the ablation catheter; providing drive signals and/or energy to one or more functional elements of the ablation catheter; providing a second energy type to the ablation elements of the ablation catheter; and combinations thereof.

In a preferred embodiment, the interface unit provides an analysis function to determine one or more system parameters that correlate to ablation settings, the parameters including but not limited to: an energy delivery amount; an energy delivery frequency; an energy delivery voltage; an energy delivery current; an energy delivery temperature; an energy delivery rate; an energy delivery duration; an energy delivery modulation parameter; an energy threshold; another energy delivery parameter; a temperature threshold; an alarm threshold; another alarm parameter; and combinations thereof. The analysis function compares a measured, calculated or otherwise determined function to a threshold value, such as a threshold value settable by an operator of the system. In a preferred embodiment, the interface unit receives temperature information from multiple sensors of the ablation catheter and/or other body inserted devices, and the highest reading received is compared to a temperature threshold such as a temperature threshold determined by the location of tissue being ablated. The analysis function includes one or more algorithms that mathematically process information such as signals received from sensors of the ablation catheter or other device; information entered into the user interface of the interface unit by the operator; embedded electronic information uploaded from the ablation catheter or other device such as information determined during the manufacture of the catheter or device; and combinations thereof. In a preferred embodiment, the ablation setting determined by the analysis function is provided to the operator via a display or other user interface output component.

The interface unit of the present invention performs one or more mathematical functions, signal processing functions; signal transmission functions; and combinations thereof, to determine a system performance (e.g. during ablation) or other system parameter. A calculation may include a function performed by an operator of the system such as a distance value that is entered into the interface unit after a measurement is performed such as a measurement made from an IVUS monitor or a fluoroscopy screen. In a preferred embodiment, energy delivered, such as a maximum cumulative energy, maximum peak energy or maximum average energy, is limited by a threshold. In a preferred embodiment, when a temperature reaches a threshold, one or more system parameters are modified. These modifications include but are not limited to: a threshold parameter such as an increased temperature threshold; an alarm or alert parameter such as an audible alarm "on" state; an energy parameter such as a parameter changing energy type or modifying energy delivery such as switching from RF energy to cryogenic energy or stopping energy delivery; a sensor parameter such as a parameter which activates one or more additional sensors; cooling apparatus parameter such as a parameter activating a cooling apparatus; a parameter that changes the polarity of energy delivery or the modulation of energy delivery such as a parameter that switches from monopolar to bipolar delivery or phased monopolar-bipolar to bipolar; and combinations thereof.

Figure 7:
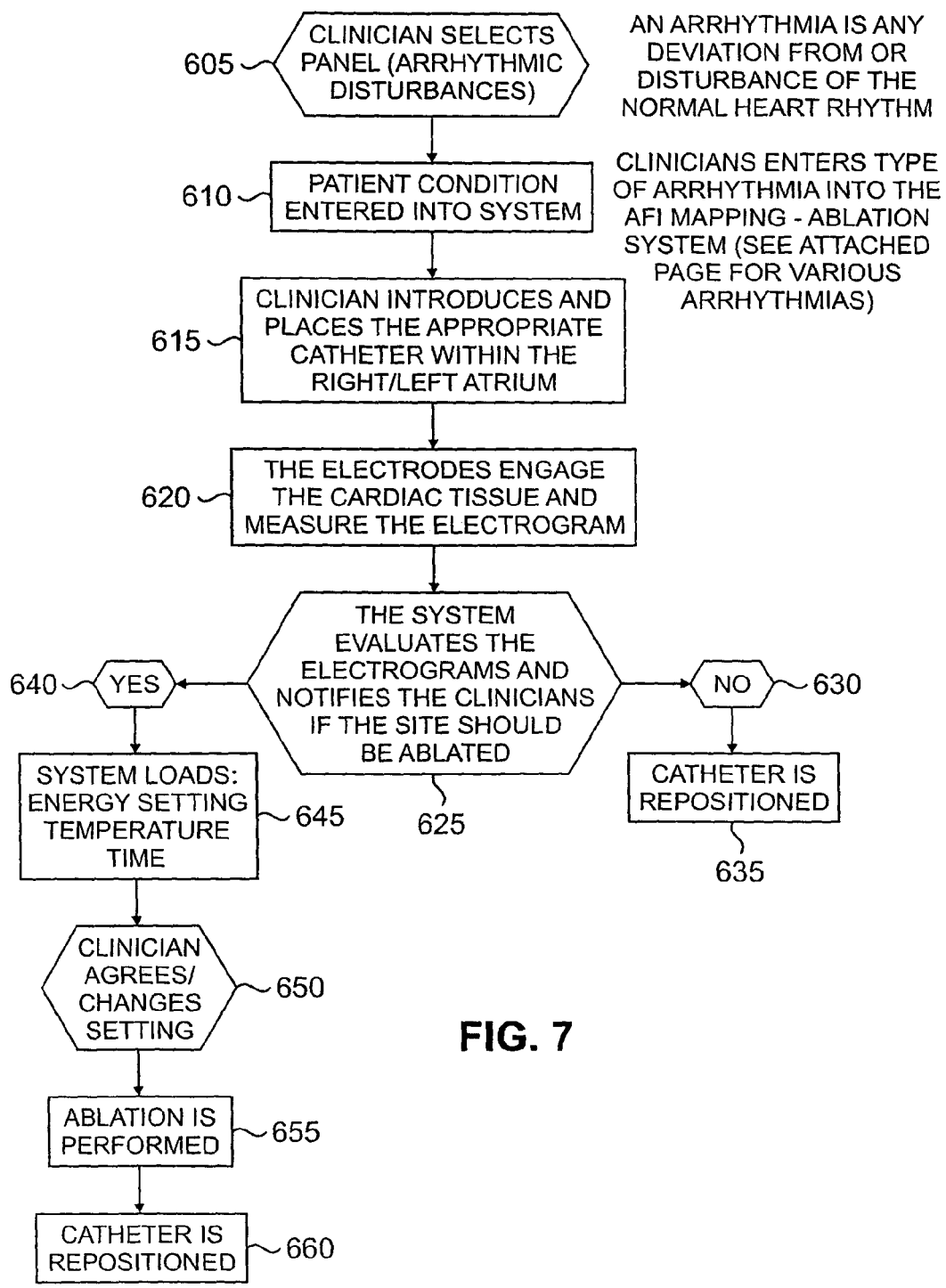
FIG. 7 is flowchart summarizing a procedure in which the ablation catheter is employed.

FIG. 7 is flowchart summarizing a procedure in which the ablation catheter is employed. In step 605 the clinican selects an appropriate patient having an arrhythmic disturbance to undergo an ablation procedure. In step 610 the various patient parameters (e.g., arrhythmia type) are entered into the system via the interface unit in the manner discussed above. In step 615 the clinician introduces the ablation catheter into the right or left atrium of the patient, as appropriate. The electrodes of the catheter engage the cardiac tissue and measure the electrogram in step 620. In decision step 625 the system evaluates the electrograms and notifies the clinician if the site should be ablated. If the system concludes that the site should not be ablated in step 630, the catheter is repositioned to evaluate another site in step 635. If, on the other hand, the system concludes in step 640, the system loads the appropriate catheter parameters such and energy, temperature and time. In step 650 the clinician reviews the parameters that have been established and either agrees with them or changes one or more of them as necessary. In step 655 ablation is performed, after which the catheter is repositioned to evaluate another site in step 660.

The system of the present invention preferably includes multiple functional elements integral to the ablation catheter and/or other system component. These functional elements may be mounted on the outer wall of the flexible shaft of the device. Alternatively or additionally, one or more functional elements may be mounted to a balloon, such as a perfusion balloon, eccentric balloon or concentric balloon and/or elements may be mounted to a carrier assembly such as a carrier assembly that exits the distal end or a side hole of the flexible shaft. These functional elements may be covered with a membrane and multiple elements may be configured in an array such as an array that is rotated within a lumen of the flexible shaft. Functional elements may be placed on the patient's chest, such as ECG electrodes, pacing electrodes or defibrillation electrodes. Functional elements include but are not limited to: sensors such as temperature sensors; transmitters such as energy transmitting electrodes, antennas and electromagnetic transmitters; imaging transducers; signal transmitters such as drive signal transmitters.

Functional elements may include sensing functions such a sensor to detect a physiologic parameter. In a preferred embodiment, one or more functional elements are configured as sensors to receive signals that are indicative of one or more cardiac functions of the patient. Sensors may include but are not limited to: an electrical signal sensor such as a cardiac electrode; a temperature sensor such as a thermocouple; an imaging transducer such as an array of ultrasound crystals; a pressure sensor; a pH sensor; a blood sensor, a respiratory sensor; an EEG sensor, a pulse oximetry sensor; a blood glucose sensor; an impedance sensor; a contact sensor; a strain gauge; an acoustic sensor such as a microphone; a photodetector such as an infrared photodetector; and combinations thereof. Functional elements alternatively or additionally include one or more transducers. The transducer may be a location element; a transmitter such as a transmitting antenna, an RF electrode, a sound transmitter; a photodiode, a pacing electrode, a defibrillation electrode, a visible or infrared light emitting diode and a laser diode; a visualization transducer such as an ultrasound crystal; and combinations thereof.

Numerous kit configurations are also to be considered within the scope of this application. An ablation catheter is provided with multiple carrier assemblies. These carrier assemblies can be removed for the tubular body member of the catheter, or may include multiple tubular body members in the kit. The multiple carrier assemblies can have different patterns, different types or amounts of electrodes, and have numerous other configurations including compatibility with different forms of energy. Multiple sensors, such as ECG skin electrodes may be included, such as electrodes that attach to the interface unit of the present invention. A kit may include one or more catheters, such as an ultrasound catheter, which are configured to enter and extend distally in a lumen of the ablation catheter. One or more esophageal probes may be included such as probes with different tip or sensor configurations.

Though the ablation device has been described in terms of its preferred endocardial and percutaneous method of use, the array may be used on the heart during open-heart surgery, open-chest surgery, or minimally invasive thoracic surgery. Thus, during open-chest surgery, a short catheter or cannula carrying the carrier assembly and its electrodes may be inserted into the heart, such as through the left atrial appendage or an incision in the atrium wall, to apply the electrodes to the tissue to be ablated. Also, the carrier assembly and its electrodes may be applied to the epicardial surface of the atrium or other areas of the heart to detect and/or ablate arrhythmogenic foci from outside the heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

The invention claimed is:

1. An ablation system, comprising:
    an ablation catheter having at least two flexible ablation elements;
    at least one electrode affixed to each ablation element reading at least one of ECG and EKG information, and transmitting energy to tissue in a monopolar mode, a bipolar mode, and a combination monopolar-bipolar mode;
    an interface unit coupled with the ablation catheter including a control interface and a visual display;
    the visual display having a graphic representation of the ablation elements, the electrodes, an electrical signal from each electrode, an indication of whether each electrode is selected to transmit energy, a current quantitative representation of a system parameter, a system parameter target value, and an indication of the selected energy mode.

2. The system of claim 1 wherein the visual display includes a touch screen display capable of selecting an electrode to receive energy.

3. The ablation system of claim 1, wherein the visual display has a controllable cursor.

4. The ablation system of claim 3, further comprising a control for controlling the controllable cursor.

5. The ablation system of claim 4, wherein the control is positioned on said interface unit.

6. The ablation system of claim 5, wherein the control is outside of a sterile field of a patient.

7. The system of claim 3 further comprising a handheld remote control device, and the controllable cursor is controlled by said handheld remote control device.

8. The ablation system of claim 1 wherein the control interface is capable of selecting multiple electrodes displayed on the visual display.

9. The ablation system of claim 1 wherein the visual display indicates a system parameter, and the interface unit is capable of changing a value of the system parameter.

10. The ablation system of claim 1 wherein the system parameter is selected from the group consisting of:
    an energy delivery parameter selected from the group consisting of: current, voltage, frequency, power, monopolar mode or bipolar mode, duration, impedance and type of energy to be delivered;
    a sensor parameter selected from the group consisting of: tissue contact measurement value; temperature, pressure, strain, impedance, ECG or EKG, cardiac flow rate, tissue thickness and tissue location;
    an alarm parameter;
    a physical catheter parameter; and
    a threshold value for a system parameter.

11. The ablation system of claim 9 wherein the visual display indicates changes in the value of said system parameter.

12. The ablation system of claim 11 wherein the system parameter is a temperature, and the visual display indicates the temperature with color.

13. The ablation system of claim 9 further comprising an audio transducer, indicating an event selected from the group of: a change in the system parameter, and the system parameter exceeding a threshold value.

14. The system of claim 1 wherein the visual display further provides a visual representation of a patient's anatomy, shown in geometric relation to the graphic representation.

15. The ablation system of claim 1 wherein the ablation catheter comprises:
    a flexible, tubular body member having a proximal end, a distal end and a lumen extending therebetween; and
    a control shaft received within the lumen of the tubular body member;
    wherein the control shaft can pull the ablation elements within the lumen of the tubular body member and can push the ablation elements distally beyond the distal end of the tubular body member.

16. The ablation system of claim 1 wherein the at least one electrode defines a triangular cross section.

* * * * *